United States Patent
Stalker et al.

(10) Patent No.: US 9,358,096 B2
(45) Date of Patent: Jun. 7, 2016

(54) METHODS OF TREATMENT WITH DRUG ELUTING STENTS WITH PROLONGED LOCAL ELUTION PROFILES WITH HIGH LOCAL CONCENTRATIONS AND LOW SYSTEMIC CONCENTRATIONS

(71) Applicant: Abbott Laboratories, Abbott Park, IL (US)

(72) Inventors: Kent C. B. Stalker, San Marcos, CA (US); Winnette S. McIntosh, San Jose, CA (US); Dudley S. Jayasinghe, Murrieta, CA (US); Gregory C. Orr, Escondido, CA (US); John E. Papp, Temecula, CA (US); Lewis B. Schwartz, Lake Forest, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/908,854

(22) Filed: Jun. 3, 2013

(65) Prior Publication Data

US 2013/0268061 A1    Oct. 10, 2013

Related U.S. Application Data

(62) Division of application No. 12/112,935, filed on Apr. 30, 2008, now abandoned.

(60) Provisional application No. 60/915,355, filed on May 1, 2007.

(51) Int. Cl.
*A61F 2/06* (2013.01)
*A61L 31/02* (2006.01)
(Continued)

(52) U.S. Cl.
CPC ............... *A61F 2/06* (2013.01); *A61L 31/022*

(58) Field of Classification Search
CPC .................................. A61L 31/16; A61F 2/06
USPC ............................................. 623/1.42, 1.46
See application file for complete search history.

(56) References Cited

U.S. PATENT DOCUMENTS

| 5,646,160 A | 7/1997 | Morris et al. |
| 5,756,553 A | 5/1998 | Iguchi et al. |

(Continued)

FOREIGN PATENT DOCUMENTS

| EP | 0 778 250 | 6/1996 |
| EP | 1 795 185 | 6/2007 |

(Continued)

OTHER PUBLICATIONS

Ramcharitar et al., "The next generation of Drug-Eluting Stents", Am. J. Cardiovasc. Drugs 7, pp. 81-93 (2007).

(Continued)

*Primary Examiner* — Thomas J Sweet
*Assistant Examiner* — Seema Mathew
(74) *Attorney, Agent, or Firm* — Squire Patton Boggs (US) LLP

(57) ABSTRACT

A drug eluting stent can include a stent body having a polymeric coating with a lipophilic and/or hydrophilic element. A drug that has a bioactivity that inhibits cell proliferation can be disposed in the polymeric coating. The drug can be present in the polymer at an amount greater than or equal to about 150 $\mu g/cm^2$. The polymeric coating and drug are configured to cooperate so as to form a diffusion pathway with tissue when the stent is disposed in a body lumen such that the drug preferentially diffuses into the tissue over a body fluid passing through the body lumen such that a maximum systemic blood concentration of the drug is less than about 40 ng/ml.

22 Claims, 7 Drawing Sheets

(51) Int. Cl.
  *A61L 31/10* (2006.01)
  *A61L 31/16* (2006.01)

(56) References Cited

U.S. PATENT DOCUMENTS

| | | | |
|---|---|---|---|
| 6,013,854 A * | 1/2000 | Moriuchi | A61F 2/91 606/194 |
| 6,015,815 A | 1/2000 | Mollison | |
| 6,042,875 A | 3/2000 | Ding et al. | |
| 6,083,257 A * | 7/2000 | Taylor et al. | 623/1.46 |
| 6,096,070 A | 8/2000 | Ragheb et al. | |
| 6,153,252 A | 11/2000 | Hossainy et al. | |
| 6,329,386 B1 | 12/2001 | Mollison | |
| 6,503,556 B2 | 1/2003 | Harish et al. | |
| 6,503,954 B1 | 1/2003 | Bhat et al. | |
| 6,540,776 B2 | 4/2003 | Sanders Millare et al. | |
| 6,555,157 B1 | 4/2003 | Hossainy | |
| 6,585,764 B2 | 7/2003 | Wright et al. | |
| 6,656,506 B1 | 12/2003 | Wu et al. | |
| 6,663,662 B2 | 12/2003 | Pacetti et al. | |
| 6,713,119 B2 | 3/2004 | Hossainy et al. | |
| 6,716,444 B1 | 4/2004 | Castro et al. | |
| 6,730,064 B2 * | 5/2004 | Ragheb et al. | 604/265 |
| 6,743,462 B1 | 6/2004 | Pacetti | |
| 6,749,626 B1 | 6/2004 | Bhat et al. | |
| 6,753,071 B1 | 6/2004 | Pacetti | |
| 6,759,054 B2 | 7/2004 | Chen et al. | |
| 6,764,505 B1 * | 7/2004 | Hossainy | A61F 2/91 427/2.25 |
| 6,780,424 B2 | 8/2004 | Claude | |
| 6,790,228 B2 | 9/2004 | Hossainy et al. | |
| 6,890,546 B2 | 5/2005 | Mollison et al. | |
| 6,896,965 B1 | 5/2005 | Hossainy | |
| 6,908,624 B2 | 6/2005 | Hossainy et al. | |
| 6,926,919 B1 | 8/2005 | Hossainy et al. | |
| 6,939,376 B2 | 9/2005 | Shulze et al. | |
| 6,994,867 B1 | 2/2006 | Hossainy et al. | |
| 7,011,842 B1 | 3/2006 | Simhambhatla et al. | |
| 7,022,372 B1 | 4/2006 | Chen | |
| 7,070,798 B1 | 7/2006 | Michal et al. | |
| 7,077,859 B2 | 7/2006 | Sirhan et al. | |
| 7,083,642 B2 | 8/2006 | Sirhan et al. | |
| 7,087,263 B2 | 8/2006 | Hossainy et al. | |
| 7,094,256 B1 | 8/2006 | Shah et al. | |
| 7,105,018 B1 | 9/2006 | Yip et al. | |
| 7,144,422 B1 | 12/2006 | Rao | |
| 7,156,869 B1 * | 1/2007 | Pacetti | A61F 2/91 606/192 |
| 7,175,873 B1 | 2/2007 | Roorda et al. | |
| 7,175,874 B1 | 2/2007 | Pacetti | |
| 7,201,935 B1 | 4/2007 | Claude et al. | |
| 7,208,190 B2 | 4/2007 | Verlee et al. | |
| 7,232,573 B1 | 6/2007 | Ding | |
| 7,247,313 B2 | 7/2007 | Roorda et al. | |
| 7,279,174 B2 | 10/2007 | Pacetti et al. | |
| 7,285,304 B1 | 10/2007 | Hossainy et al. | |
| 7,294,329 B1 | 11/2007 | Ding | |
| 7,318,932 B2 | 1/2008 | Pacetti | |
| 7,329,366 B1 | 2/2008 | Gale et al. | |
| 7,329,413 B1 | 2/2008 | Pacetti et al. | |
| 7,357,942 B2 | 4/2008 | Burke et al. | |
| 7,363,074 B1 | 4/2008 | Kwok et al. | |
| 7,364,748 B2 | 4/2008 | Claude | |
| 7,378,105 B2 | 5/2008 | Burke et al. | |
| 7,390,497 B2 | 6/2008 | DesNoyer et al. | |
| 7,390,523 B2 | 6/2008 | Pacetti et al. | |
| 7,396,539 B1 | 7/2008 | Hossainy et al. | |
| 7,399,480 B2 | 7/2008 | Mollison et al. | |
| 7,413,574 B2 | 8/2008 | Yip et al. | |
| 7,413,746 B2 | 8/2008 | Ding | |
| 7,416,558 B2 | 8/2008 | Yip et al. | |
| 7,431,959 B1 | 10/2008 | Dehnad | |
| 7,445,792 B2 | 11/2008 | Toner et al. | |
| 7,481,835 B1 | 1/2009 | Pacetti et al. | |
| 7,645,474 B1 | 1/2010 | Pathak et al. | |
| 7,645,504 B1 | 1/2010 | Pacetti | |
| 7,727,275 B2 | 6/2010 | Betts et al. | |
| 7,776,926 B1 | 8/2010 | Claude et al. | |
| 7,785,512 B1 | 8/2010 | Pathak | |
| 8,349,249 B2 | 1/2013 | Wachter et al. | |
| 8,551,512 B2 | 10/2013 | Hossainy et al. | |
| 2002/0082679 A1 | 6/2002 | Sirhan et al. | |
| 2002/0133183 A1 | 9/2002 | Lentz et al. | |
| 2002/0188277 A1 | 12/2002 | Roorda et al. | |
| 2003/0033007 A1 | 2/2003 | Sirhan et al. | |
| 2003/0050692 A1 * | 3/2003 | Sirhan | A61F 2/91 623/1.42 |
| 2003/0097088 A1 | 5/2003 | Pacetti | |
| 2003/0125800 A1 | 7/2003 | Shulze et al. | |
| 2003/0229392 A1 * | 12/2003 | Wong | A61F 2/06 623/1.42 |
| 2004/0033250 A1 * | 2/2004 | Patel | A61K 9/0024 424/423 |
| 2004/0052858 A1 | 3/2004 | Wu et al. | |
| 2004/0052859 A1 | 3/2004 | Wu et al. | |
| 2004/0072922 A1 | 4/2004 | Hossainy et al. | |
| 2004/0142015 A1 | 7/2004 | Hossainy et al. | |
| 2004/0158309 A1 | 8/2004 | Wachter et al. | |
| 2004/0162609 A1 | 8/2004 | Hossainy et al. | |
| 2004/0220665 A1 | 11/2004 | Hossainy et al. | |
| 2004/0249444 A1 * | 12/2004 | Reiss | B23H 9/008 623/1.15 |
| 2005/0033261 A1 * | 2/2005 | Falotico | A61F 2/91 604/500 |
| 2005/0038500 A1 | 2/2005 | Boylan et al. | |
| 2005/0112172 A1 | 5/2005 | Pacetti | |
| 2005/0119720 A1 | 6/2005 | Gale et al. | |
| 2005/0125054 A1 | 6/2005 | Bhat et al. | |
| 2005/0187376 A1 | 8/2005 | Pacetti | |
| 2005/0203612 A1 * | 9/2005 | Bhat | A61F 2/90 623/1.42 |
| 2005/0208093 A1 | 9/2005 | Glauser et al. | |
| 2005/0222676 A1 * | 10/2005 | Shanley | A61F 2/91 623/1.42 |
| 2005/0232971 A1 | 10/2005 | Hossainy et al. | |
| 2005/0238686 A1 | 10/2005 | Hossainy et al. | |
| 2005/0244363 A1 | 11/2005 | Hossainy et al. | |
| 2005/0245637 A1 | 11/2005 | Hossainy et al. | |
| 2005/0266038 A1 | 12/2005 | Glauser et al. | |
| 2005/0271700 A1 | 12/2005 | DesNoyer et al. | |
| 2005/0287184 A1 | 12/2005 | Hossainy et al. | |
| 2006/0002974 A1 | 1/2006 | Pacetti et al. | |
| 2006/0004441 A1 * | 1/2006 | Tijsma | A61F 2/07 623/1.42 |
| 2006/0062821 A1 | 3/2006 | Simhambhatla et al. | |
| 2006/0078493 A1 * | 4/2006 | von Oepen | A61F 2/82 424/1.11 |
| 2006/0078588 A1 | 4/2006 | Hossainy | |
| 2006/0106453 A1 | 5/2006 | Sirhan et al. | |
| 2006/0115449 A1 | 6/2006 | Pacetti | |
| 2006/0121080 A1 * | 6/2006 | Lye | A61F 2/07 623/1.39 |
| 2006/0198867 A1 | 9/2006 | Toner et al. | |
| 2006/0198870 A1 | 9/2006 | Mollison et al. | |
| 2006/0287709 A1 | 12/2006 | Rao | |
| 2007/0016284 A1 | 1/2007 | Pacetti | |
| 2007/0032853 A1 | 2/2007 | Hossainy et al. | |
| 2007/0032858 A1 | 2/2007 | Santos et al. | |
| 2007/0110787 A1 | 5/2007 | Hossainy et al. | |
| 2007/0116857 A1 | 5/2007 | Pacetti | |
| 2007/0202323 A1 | 8/2007 | Kleiner et al. | |
| 2007/0250157 A1 * | 10/2007 | Nishide | A61F 2/91 623/1.42 |
| 2007/0276488 A1 | 11/2007 | Wachter et al. | |
| 2007/0280988 A1 | 12/2007 | Ludwig | |
| 2008/0003254 A1 | 1/2008 | Mack et al. | |
| 2008/0004694 A1 | 1/2008 | Mack et al. | |
| 2008/0004695 A1 | 1/2008 | Stewart | |
| 2008/0086198 A1 * | 4/2008 | Owens | A61F 2/91 623/1.39 |
| 2008/0087283 A1 | 4/2008 | Cromack et al. | |
| 2008/0097591 A1 * | 4/2008 | Savage | A61F 2/91 623/1.43 |
| 2008/0132989 A1 * | 6/2008 | Snow et al. | 623/1.12 |

(56) References Cited

U.S. PATENT DOCUMENTS

| | | | |
|---|---|---|---|
| 2008/0145402 | A1 | 6/2008 | Mollison et al. |
| 2008/0153790 | A1 | 6/2008 | Mollison et al. |
| 2008/0171763 | A1 | 7/2008 | Mollison et al. |
| 2008/0175884 | A1 | 7/2008 | Mollison et al. |
| 2008/0188924 | A1* | 8/2008 | Prabhu ............... A61F 2/82 623/1.16 |
| 2008/0195189 | A1* | 8/2008 | Asgari ............... A61L 31/022 623/1.2 |
| 2008/0249608 | A1* | 10/2008 | Dave ............... A61F 2/91 623/1.16 |
| 2009/0024199 | A1* | 1/2009 | Birdsall ............... A61F 2/91 623/1.11 |
| 2010/0104734 | A1 | 4/2010 | Orosa et al. |
| 2010/0241214 | A1* | 9/2010 | Holzer ............... A61F 2/07 623/1.15 |
| 2010/0274349 | A1* | 10/2010 | Lord ............... B26D 7/14 623/1.16 |
| 2010/0305689 | A1* | 12/2010 | Venkatraman ............ A61F 2/91 623/1.46 |
| 2010/0323093 | A1* | 12/2010 | Chen ............... A61F 2/91 427/2.25 |
| 2011/0137407 | A1* | 6/2011 | Nguyen ............... A61F 2/91 623/1.42 |
| 2011/0144578 | A1* | 6/2011 | Pacetti et al. ............. 604/96.01 |
| 2012/0165923 | A1* | 6/2012 | Maruyama ............ A61F 2/915 623/1.42 |
| 2014/0135286 | A1* | 5/2014 | McKay ............... A61K 31/737 514/59 |
| 2014/0194533 | A1* | 7/2014 | Hsu ............... A61L 27/165 514/772.3 |
| 2014/0205740 | A1 | 7/2014 | Orosa et al. |
| 2014/0296967 | A1* | 10/2014 | Bureau ............... A61L 31/10 623/1.42 |
| 2016/0030155 | A1* | 2/2016 | Cox ............... A61F 2/07 623/1.13 |

FOREIGN PATENT DOCUMENTS

| | | |
|---|---|---|
| WO | WO 94/09010 | 4/1994 |
| WO | WO 03/082368 | 10/2003 |
| WO | WO 2004/010900 | 2/2004 |
| WO | WO 2004/026359 | 4/2004 |
| WO | WO 2008/011093 | 1/2008 |
| WO | WO 2008/137547 A1 | 11/2008 |

OTHER PUBLICATIONS

International Search Report for PCT/US2008/062220, mailed Sep. 30, 2008, 3 pgs.
Duda et al., Drug-Eluting and Bare Nitinol Stents for the Treatment of Atherosclerotic Lesions in the Superifical Femoral Artery: Long-term Results from the SIROCCP Trial, J. Endovasc Ther, 2006, vol. 13, pp. 701-710.
Duda et al., "Sirolimus-Eluting Stents for the Treatment of Obstructive Superficial Femoral Artery Disease", Circulation, Sep. 17, 2002, vol. 106, pp. 1505-1509.
Duda et al., "Sirolimus-Eluting versus Bare Nitinol Stent for Obstructive Superficial Femoral Artery Disease: The SIROCCO II Trial", J Vasc Interv Radiol, Mar. 2005, vol. 16, No. 3, pp. 331-338.
Written Opinion of the International Searching Authority for International application No. PCT/US2008/062220 mailed Sep. 30, 2008, 7 pages.
Adam, D. J. et al., "Bypass versus angioplasty in severe ischaemia of the leg (BASIL): multicentre, randomised controlled trial", The Lancet, Dec. 3, 2005, vol. 366, No. 9501, pp. 1925-1934.
Allie, David E. et al., "Nitinol stent fractures in the SFA", Endovascular Today, Jul./Aug. 2004, pp. 22-34.
Ascher, Enriko et al., "Duplex-guided endovascular treatment for occlusive and stenotic lesions of the femoral-popliteal arterial segment: A comparative study in the first 253 cases", J. Vasc. Surg. 2006, vol. 44, No. 6, pp. 1230-1238.
Becquemin, Jean-Pierre et al., "Systematic versus selective stent placement after superficial femoral artery balloon angioplasty: A multicenter prospective randomized study", J. Vasc. Surg., Mar. 2003, vol. 37, pp. 487-494.
Budde, Klemens et al., "Tolerability and steady-state pharmacokinetics of everolimus in maintenance renal transplant patients", Nephrol Dial Transplant, 2004, vol. 19, No. 10, pp. 2606-2614.
Bui, Trung D. et al., "Transluminal stenting for femoropopliteal occlusive disease: Analysis of restenosis by serial arteriography", Ann. Vase. Surg. 2006, vol. 20, No. 2, pp. 200-208.
Carter, Andrew J. et al., "Experimental efficacy of an everolimus eluting cobalt chromium stent", Cath. Cardiovasc. Interv., 2006, vol. 68, pp. 97-103.
Cejna, Manfred et al., "PTA versus Palmaz stent placement in femoropopliteal ariery obstructions: a multicenter prospective randomized study", J. Vasc. Interv. Radiol, 2001, vol. 12, pp. 23-31.
Cheng, Stephen W.K. et al., "Angioplasty and primary stenting of high-grade, long-segment superficial femoral artery disease: Is it worthwhile?" Ann. Vasc. Surg., 2003, vol. 17, No. 4, pp. 430-437.
Clark, David J. et al., "Mechanisms and Predictors of Carotid Artery Stent Restenosis: A Serial Intravascular Ultrasound Study", J. Am. Coli. Cardiol. Jun. 20, 2006, vol. 47, No. 12, pp. 2390-2396.
Costa, Ricardo A. et al., "Angiographic analysis of stent fracture in superficial femoral artery (SFA) or proximal popliteal artery lesions treated with the S.M.A.R.T. nitinol selfexpanding stent and relationship to adverse clinical events (abstract)", Am. J. Cardio. 2005, Supplement to vol. 96, No. 7, p. 20H.
Costanza, Michael J. et al., "Hemodynamic outcome of endovascular therapy for TransAtlantic Inter Society Consensus type B femoropopliteal artedal occlusive lesions", J. Vasc. Surg., Feb. 2004, vol. 39, No. 2, pp. 343-350.
Diehm, Nicholas et al., "Endovascular brachytherapy after femoropopliteal balloon angioplasty fails to show robust clinical benefit over time", J. Endovasc. Ther. 2005, vol. 12, pp. 723-730.
Dunn, Christopher et al., "Everolimus: A review of its use in renal and cardiac transplantation", Drugs, 2006, vol. 66, No. 4, pp. 547-570.
Duvall, M. et al., "ABT-578 elution profile and arterial penetration using the ZoMaxx drug-eluting stent," (abstract), Am. J. Cardiol, Sep. 20, 2004, 1 page, p. 223E.
Eisen, Howard J. et al., "Everolimus for the prevention of allograft rejection and vasculopathy in cardiac-transplant recipients", New Engl. J. Med., Aug. 28, 2003, vol. 349, No. 9, pp. 847-858.
Farb, Andrew et al., "Oral everolimus inhibits in-stent neointimal growth", Circulation, Oct. 29, 2002, vol. 106, pp. 2379-2384.
Grant, A.G. et al., "Infrapopliteal drug-eluting stents for chronic limb ischemia", Cath. Cardiovasc. Interv. 2008, vol. 71, pp. 108-111.
Gray, Bruce H. et al., "High incidence of restenosis/reocclusion of intravascular stents in the percutaneous treatment of long-segment superficial femoral artery disease after suboptimal angioplasty", J. Vasc. Surg., 1997, vol. 25, No. 1, pp. 74-83.
Grube, Eberhard et al., Six- and twelve-month results fro first human experience using everolimus-eluting stents with bioabsorbable polymer, Circulation, 2004, vol. 109, pp. 2168-2171.
Hirsch, Alan T. et al., "ACC/AHA 2005 guidelines for the management of patients with peripheral arterial disease (lower extremity, renal, mesenteric, and abdominal aortic): Executive Summary, A collaborative report from the American Association for Vascular Surgery/Society for Vascular Surgery, Society for Cardiovascular Angiography and Interventions, Society for Vascular Medicine and Biology, Society of interventional Radiology, and the ACC/AHA Task Force on Practice, Guidelines (writing committee to develop guidelines for the management of patients with peripheral arterial disease)", J. Am. Coll. Cardio, 2006, vol. 47, No. 6, pp. 1239-1312.
Iida, Osamu et al., "Effect of exercise on frequency of stent fracture in the superficial femoral artery", Am. J. Cardiol., 2006, vol. 98, pp. 272-274.
Kandzari, David E. et al., "Comparison of zotarolimus-eluting and sirolimus-eluting stents in patients with native coronary artery disease: A randomzied controlled trial," J. Am. Coll. Cardiol. Dec. 19, 2006, vol. 48, No. 12, pp. 2440-2447.
Kirchner, Gabriele I. et al., "Clinical phannacokinetics of everolimus", Clin. Pharmacokinet, 2004, vol. 43, No. 2, pp. 83-95.

(56) References Cited

OTHER PUBLICATIONS

Kirsch, Eberhard C. et al., "Oversizing of self-expanding stents: influence on the development of neointimal hyperplasia of the carotid artery in a canine model", Am. J. Neuroradiol., Jan. 2002, vol. 23, pp. 121-127.
Krankenberg, Hans et al., Nitinol Stent Implation Versus Percutaneous Transluminal Angioplasty in Superficial Femoral Artery Lesions up to 10cm in Length, The Femoral Artery Stenting Trial, Jul. 17, 2007, Circulation, pp. 285-292.
Krankenberg, Hans et al., "Percutaneous revasculmization of long chronic occlusion of the superficial femoral miery—a pilot study." Dtsch. Med. Wschr. 2001, vol. 126, No. 17, pp. 491-495.
Laird, John et al., "Cryoplasty for the treatment of femoropopliteal arterial disease: Results of a prospective, multicenter registry", J. Vasc. Interv. Radiol., 2005, vol. 16, No. 8, pp. 1067-1073.
Laird, John R. et al., "Nitinol Stent Implatation Versus Baloon Agioplasty for Lesions in the Superficial Femoral Artery and Proximal Popliteal Artery, Twelve-Month Results from the RESILIENT Randomized Trial," Circ. Cardiovasc. Interv., 2010, vol. 3, pp. 267-276.
Lansky, Alexandra J. et al., "Nonpolymer-based paclitaxel-coated coronary stents for the treatment of patients with de novo coronary lesions: Angiographic follow-up of the DELIVER Clinical Trial", Circulation, 2004, vol. 109, pp. 1948-1954.
Lugmayr, Herbert F. et al., "Treatment of complex arthetiosclerotic lesions with nitinol stents in the superficial femoral and popliteal arieries: A mid-term follow-up", Radiology, 2002, vol. 222, No. 1, pp. 37-43.
Mewissen, Mark W., "Self-expanding nitinol stents in the femoropopliteal segment: technique and mid-term results", Techniques in Vascular and Interventional Radiology, Mar. 2004, vol. 7, No. 1, pp. 2-5.
Moses, Jeffrey W. et al., "Sirolimus-eluting stents versus standard stents in patients with stenosis in a native coronary artery", New Engl. J. Med., Oct. 2, 2003, vol. 349, No. 14, pp. 1315-1323.
Mureebe, Leila et al., "Infrainguinal artetial intervention: is there a role for an atherectomy device?", Vascular 2006, vol. 14, No. 5, pp. 313-318.
Nikanorov, Alexander et al., "Fracture of self-expanding nitinol stents stressed in-vitro under simulated intravascular conditions", J. Vasc. Surg. Aug. 2008, vol. 48, pp. 435-440.
Pentecost, Michael J. et al., "Guidelines for peripheral percutaneous transluminal angioplasty of the abdominal aorta and lower extremity vessels: A statement for health professionals from a special wdting group of the Councils on Cardiovascular Radiology, Arteriosclerosis, Cardia-Thoracic and Vascular Surgery, Clinical Cardiology, and Epidemiology and Prevention, the American Heart Association", J. Vasc. Interv. Radiol, Sep. 2003, vol. 14, pp. S495-S515.
Piamsomboon, Chumpoi et al., "Relationship between oversizing of self-expanding stents and late loss index in carotid stenting", Cathet. Cardiovasc. Diagn., Oct. 1998, vol. 45, No. 2, pp. 139-143.
PRNewswire, "15,000-Patient Interventional Cardiology Registry to Evaluate Impact of Drug-Eluting Corornary Stents: The Cordissponsored 'D.E.S.cover Registry' to Include More Than 200 U.S. Hospitals", COMTEX, Jan. 19, 2004, 1 page.
PRNewswire, "Enrollment Complete in First Randomized Head-toHead Trial of Drug-eluting Coronary Stents: REALITY Trial to Compare Performance in Diabetics and Other High-Risk Patients", COMTEX, Feb. 18, 2004, 2 pages.
Rapamune (sirolimus) oral solution and tablets, Wyeth Laboratoires, Division of Wyeth-Ayerst Pharmaceuticals Inc., Philadelphia, Pennsylvania, 2003 pp. 1-37.
Sabeti, Schila et al., "Primary patency of long-segment self-expanding Nitinol stents in the femoropopliteal arteries", J. Endovasc. Ther. 2005, vol. 12, pp. 6-12.
Sabeti, Schila et al., "Quality of life after balloon angioplasty versus stent implantation in the superficial femoral artery: Findings from a randomized controlled trial," J. Endovasc. Ther. 2007, vol. 14 pp. 431-437.
Scheinert, Dierk et al., "Prevalence and clinical impact of stent fractures after femoropopliteal stenting", J. Am. Col. Cardio., 2005, vol. 45, No. 2, pp. 312-315.
Scheinert, Dierk et al., "Comparison of sirolimus-eluting vs. baremetal stents for the treatment of infrapopliteal obstructions", EuroInterv., 2006, vol. 2, pp. 169-174.
Schillinger, Martin et al., "Balloon angioplasty versus implantation of nitinol stents in the superficial femoral artery", New Engl. J. Med., May 4, 2006, vol. 354, No. 18, pp. 1879-1888.
Schillinger, Martin et al., "Sustained benefit at two years of primary femoropopliteal stenting compared with balloon angioplasty with optional stenting", Circulation, May 29, 2007, vol. 115, No. 21, pp. 2745-2749.
Schlager, Oliver et al., "Long-segment SFA stenting—the dark sides: in-stent restenosis, clinical deterioration, and stent fractures", J. Endovasc. Ther. 2005, vol. 12, pp. 676-684.
Serruys, Patrick W. et al., "A randomised comparison of an everolimus-eluting coronary stent with a paclitaxeleluting coronary stent: the SPIRIT II trial", EuroInterv. 2006, vol. 2, pp. 286-294.
Serruys, Patrick W. et al., "A randomized comparison of a durable polymer everolimus-eluting stent with a bare metal coronary stent: The SPIRIT first trial", EuroInterv., May 2005, vol. 1, No. 1, pp. 58-65.
Serruys, Patrick W. et al., "Coronary-artery stents", New Engl. J. Med., Feb. 2, 2006, vol. 354, No. 5, pp. 483-495.
Siablis, Dimitris et al., "Infrapopliteal application of paclitaxel-eluting stents for critical limb ischemia: Midterm angiographic and clinical results", J. Vasc. Interv. Radiol., Nov. 2207, vol. 18, pp. 1351-1361.
Stone, Gregg W., "Clinical, angiographic and IVUS results from the Pivotal U.S. randomized SPIRIT III Trial of the XIENCE V everolimus-eluting coronary stent system", American College of Cardiology, New Orleans, Louisiana, Mar. 2007, 31 pages.
Surowiec, Scott M. et al., "Percutaneous angioplasty and stenting of the superficial femoral artery," J. Vasc. Surg. Feb. 2005, vol. 41, No. 2, pp. 269-278.
Tepe, Gunnar et al., "Superficial femoral artery: current treatment options", Eur. Radiol., 2006, vol. 16, pp. 1316-1322.
Tsuchiya, Yoshihiro et al., "Effect of everolimus-eluting stents in different vessel sizes (from the Pooled FUTURE I and II Trials)", Am. J. Cardiol., 2006, vol. 98, pp. 464-469.
van der Zaag, E.S. et al., "Angioplasty or bypass for superficial femoral artery disease? A randomised controlled trial", Eur. J. Vasc. Endovasc. Surg. 2004, vol. 28, pp. 132-137.
Vetrovec, George W. et al., "Sirolimus PK trial: a pharmacokinetic study of the sirolimus-eluting Bx velocity stent in patients with de novo coronary lesions", Cath. Cardiovasc. Interv., 2006, vol. 67, pp. 32-37.
Vorwerk, Dierk et al., "Neointima formation following arterial placement of self-expanding stents of different radial force: experimental results", Cardiovasc. Intervent. Radiol, Jan./Feb. 1994, vol. 17, No. 1, pp. 27-32.
Waksman, Ron et al., "Optimal dosing and duration of oral everolimus to inhibit in-stent neointimal growth in rabbit iliac arteries", Cardiovasc. Revasc. Med., May 2006, vol. 7, pp. 179-184.
White, Christopher et al., "Endovascular therapies for peripheral artedal disease: An evidence-based review", Circulation, Nov. 6, 2007, vol. 116, pp. 2203-2215.
Yamaguchi, Masato et al., "Placement of self-expanding Stents with Different Diameters in the Porcine Venous System: An Experimental Study", J. Vasc. Interv. Radiol., 2006, vol. 17, pp. 113-119.
Zamora, Carlos Armando et al., "Effect of stent oversizing on in-stent stenosis and lumen size in normal porcine veins", J. Endovasc. Ther., Aug. 2005, vol. 12, No. 4, pp. 495-502.

* cited by examiner

METHODS OF TREATMENT WITH DRUG ELUTING STENTS WITH PROLONGED LOCAL ELUTION PROFILES WITH HIGH LOCAL CONCENTRATIONS AND LOW SYSTEMIC CONCENTRATIONS

CROSS-REFERENCE TO RELATED APPLICATIONS

This U.S. Patent Application is a division of U.S. patent application Ser. No. 12/112,935, filed on Apr. 30, 2008, and published as U.S. Patent Application Publication Number 2009-0093875 A1, on Apr. 9, 2009, which is incorporated by specific reference herein in its entirety, including any drawings, and is incorporated by reference herein for all purposes; and U.S. patent application Ser. No. 12/112,935 claims benefit of U.S. Provisional Patent Application having Ser. No. 60/915,355, filed on May 1, 2007, which Provisional Patent Application is incorporated herein by specific reference in its entirety.

BACKGROUND OF THE INVENTION

1. The Field of the Invention

The present invention generally relates to a polymer/drug-coated stent. More particularly, the polymer/drug-coated stent is configured have the drug disposed within the polymer coating in a manner that controls the elution of the drug so as to preferentially deliver the drug into vascular tissue adjacent to the stent while maintaining a sufficiently low systemic concentration range of the drug below a specified value.

2. The Relevant Technology

Endovascular techniques have become important adjuncts in the management of atherosclerotic occlusive disease. Once amendable only to open surgical revascularization, a wide range of lesions can now be approached percutaneously without the need for incision and dissection. Endovascular interventions within coronary arteries are particularly effective, and have become the preferred method of treatment for the majority of patients with occlusive syndromes of the coronary circulation.

Endovascular intervention in the peripheral circulation has proven more problematic. Although generally effective in the relatively large inflow arteries of the extracranial cerebrovascular, renal and iliac circulations, endovascular manipulation of the infrainguinal arteries is technically more challenging, and the outcome less durable.

A variety of approaches have been suggested to enhance patency during peripheral endovascular intervention including pharmacotherapy, stenting, cryoplasty, cutting balloon angioplasty, radiation brachytherapy and atherectomy. The most popular to date is stenting, as results from a recent randomized clinical trial suggest that routine nitinol stenting enhances both angiographic and clinical results following balloon angioplasty, especially in patients with long, complex occlusive lesions of the superficial femoral artery (SFA).

However, the long-term results of stenting in the peripheral vasculature continue to be plagued by restenosis. Restenosis, mediated by the pathological process of neointimal hyperplasia, complicates roughly 40% of all peripheral vascular interventions after one year, leading a recent international consensus panel of cardiologists, vascular surgeons, and interventional radiologists to suggest that the current state-of-the-art of SFA stenting results in only 62% patency after one year.

As significant enhancements in stented arterial patency have been achieved in the coronary circulation through the use of drug-eluting stents (DES), it was natural that this technology would be eventually applied to the peripheral circulation. Several small series have been published that suggest that drug-eluting stents designed for the coronary arteries might also be efficacious in limiting restenosis and improving patency in the infrapopliteal arteries. Similarly, the hypothesis that drug-eluting stents might also be efficacious in the larger and more complex SFA was previously addressed. Also, self-expanding drug-eluting stents utilized a nitinol platform, was loaded with 90 µg sirolimus/cm$^2$ stent area using a 5-10 µm co-polymer matrix for total drug load ~1 mg per 80 mm stent (i.e., stent 1), and delivered its drug load over a period of about seven days. A total of 93 patients were enrolled in combined clinical trials for the stent. Unfortunately, neither trial achieved its primary endpoint of a reduction in restenosis and, even after four years, there was no difference in any metric comparing patients treated with the bare nitinol stent vs. the sirolimus-eluting nitinol stent. The development of this drug-eluting stent was terminated, and no drug-eluting stent is yet available for clinical use anywhere in the world.

In retrospect, some have hypothesized that the failure of the drug-eluting stent design (e.g., stent 1) was in its inadequate drug delivery. As stated, Stent 1 was loaded with 90 µg sirolimus/cm$^2$ stent area which was lower that one successful sirolimus-eluting coronary stent (e.g., stent 2), which had 140 µg sirolimus/cm$^2$ stent area. Moreover, stent 1 released sirolimus over about seven days, which is considerably shorter than the 30 day release of stent 2, both being insufficient in duration for intended therapeutic purposes. As coronary stents with short elution profiles are generally less efficacious than their longer-eluting counterparts, it was perhaps not surprising that stent I failed to demonstrate efficacy in reducing restenosis.

A second observation made from the aforementioned studies was that large peripheral drug-eluting stents with relatively high drug loads and fast elution can subsequently generate significant levels of drug in the systemic circulation. These systemic levels of drug can be considered unsafe and may have adverse side effects. In any event, high systemic levels of drug is not advantageous and may counteract the intended therapy. Some coronary drug-eluting stents, with their minimal drug loads (~100 µg), generate little in the way of systemic drug concentration; whole blood levels exceeding 2 ng/ml are rarely observed. In contrast, large peripheral drug-eluting stents carry drug loads in the milligram (mg) range, and thereby have extremely fast drug elution that increases systemic concentration of the drug and may result in adverse systemic drug exposure. Such was the case in the aforementioned trial in which treated patients exhibited a mean systemic sirolimus concentration of 20.4±10.0 ng/ml one hour after stenting, including one patient with a peak concentration of 35.5 ng/ml sirolimus after receiving three 80 mm stents configured as stent 1. These concentrations are measurably higher than the 9 ng/ml trough concentration observed in kidney transplant recipients receiving the usual oral dose of sirolimus of 2 mg per day. These high systemic drug concentrations have been deemed excessive in terms of adverse effects that may occur by long-term exposure to high systemic drug concentrations.

Lastly, a final unexpected consequence of the aforementioned trial, and a possible reason for its failure, was the observation that the stent platform was prone to fracture. Of the 93 patients enrolled, stent fracture was found in 18% at six months, including single strut fractures in eight patients, multiple strut fractures in four patients, complete transverse linear stent separations in two patients, and transverse linear fractures with stent displacement in two patients. It has been suggested that stent fracture may create a nidus for restenosis, given the documented association between strut fracture, restenosis and therapeutic failure. Indeed, the reported frequency of strut fracture following peripheral stenting is surprisingly high, including one retrospective clinical study demonstrating a fracture rate of 65%.

BRIEF SUMMARY OF THE INVENTION

Generally, the present invention includes a polymer/drug-coated stent. The polymer/drug-coated stent is configured have the drug disposed within the polymer coating in a manner that controls the elution of the drug so as to preferentially deliver the drug into vascular tissue adjacent to the stent while maintaining a sufficiently low systemic concentration of the drug.

In one embodiment, the present invention can include a drug eluting stent that has a stent body, a polymeric coating, and an lipophilic drug. The polymeric coating can have a lipophilic element and be disposed on the stent body. The lipophilic drug can have a bioactivity that inhibits cell proliferation, and can be disposed in the polymeric coating. However, any lipophilic drug with any activity can be used for the treatment of an appropriate condition.

In one embodiment, the present invention can include a drug eluting stent that has a stent body, a polymeric coating, and a hydrophilic drug. The polymeric coating can have a hydrophilic element and be disposed on the stent body. For example, the hydrophilic drug can have a bioactivity that inhibits cell proliferation, and can be disposed in the polymeric coating. However, any hydrophilic drug with any activity can be used for the treatment of an appropriate condition.

In one embodiment, the present invention can include a drug eluting stent that has a stent body, a polymeric coating, and an amphipathic drug having both hydrophilic and lipophilic components. The polymeric coating can have a hydrophilic and/or hydrophilic element and be disposed on the stent body. For example, the amphipathic drug can have a bioactivity that inhibits cell proliferation, and can be disposed in the polymeric coating. However, any amphipathic drug with any activity can be used for the treatment of an appropriate condition.

In one embodiment, the drug can be present in the polymer at an amount from about 10 $\mu g//cm^2$ (micrograms drug/area of stent) to about 2000 $\mu g/cm^2$, more preferably from about 100 $\mu g/cm^2$ to about 1000 $\mu g/cm^2$, and most preferably from about 200 $\mu g/cm^2$ to about 500 $\mu g/cm^2$.

In one embodiment, the drug per area can be greater or equal to about 150 $\mu g/cm^2$, more preferably greater or equal to about 175 $\mu g/cm^2$, even more preferably greater or equal to about 200 $\mu g/cm^2$, and most preferably greater or equal to about 225 $\mu g/cm^2$.

In one embodiment, the amount of drug on the stent can be described as the total amount of drug per stent. Accordingly, the amount of drug per stent can be from about 0.5 mg to about 12 mg, more preferably from about 0.75 mg to about 10 mg, and most preferably from about 1 mg to about 5 mg.

The polymeric coating and drug are configured to cooperate so as to form a lipophilic diffusion pathway with tissue when the stent is disposed in a body lumen such that the lipophilic drug preferentially diffuses into the tissue over a body fluid passing through the body lumen such that a maximum systemic blood concentration of the drug is less than or about 30 ng/ml, more preferably less than or about 20 ng/ml, and most preferably less than or about 10 ng/ml.

In one embodiment, the stent body is comprised of a superelastic alloy, such as nitinol. The nitinol can have an ethylenevinylalcohol copolymer coating disposed thereon. A therapeutically effective amount of everolimus can be disposed in the polymeric coating so as to be present at an amount greater than or equal to about 150 $\mu g/cm^2$. The polymer coating and everolimus are configured so as to cooperate to form a lipophilic diffusion pathway with tissue when the stent is disposed in a body lumen such that the everolimus preferentially diffuses into the tissue over a body fluid passing through the body lumen and such that a maximum systemic blood concentration of everolimus is less than about 40 ng/ml.

In one embodiment, the present invention includes a method of inhibiting occlusion, stenosis, restenosis, or cell over-proliferation in a body lumen in a subject. Such a method includes providing a stent as described herein and deploying the drug eluting stent into the body lumen.

In one embodiment, the present invention includes a method of manufacturing a stent in accordance with the present invention. Such a method includes preparing a stent body, preparing a polymer/drug solution, and applying the polymer/drug solution to the stent body. Alternatively, the polymer and drug can be applied to the stent separately. Additionally, a polymeric topcoat can be applied over the polymeric coating that has the drug.

In one embodiment, the drug eluting stent produces a systemic blood concentration of the drug that in turn produces at least one of the following: a maximum kidney concentration of less than or about 50 ng/g, more preferably less than or about 40 ng/g, and most preferably less than or about 30 ng/g; a maximum lung concentration of less than or about 45 ng/g, more preferably less than or about 35 ng/g, and most preferably less than or about 25 ng/g; a maximum muscle concentration of less than or about 35 ng/g, less than or about 30 ng/g, and most preferably less than or about 25 ng/g; a maximum liver concentration of less than or about 30 ng/g, more preferably less than or about 25 ng/g, and most preferably less than or about 17 ng/g; or a maximum spleen concentration of less than or about 35 ng/g, more preferably less than or about 30 ng/g, and most preferably less than or about 25 ng/g.

In one embodiment, the maximum systemic blood concentration of the drug is less than about 4 ng/ml per milligram of total drug on the stent.

In one embodiment, the maximum systemic blood concentration of the drug is less than about 15 pg/ml per millimeter of stent length.

In one embodiment, the stent is characterized by at least one of the following: the drug is present at greater than or about 3.8 mg; the maximum systemic blood concentration is from about 0.6 ng/ml to about 15 ng/ml; the drug is present at greater than or about 7.5 mg; the maximum systemic blood concentration is from about 1.5 ng/ml to about 30 ng/ml; the drug is present at greater than or about 10 mg; or the maximum systemic blood concentration is from about 2 ng/ml to about 40 ng/ml.

In one embodiment, the polymeric coating ranges from about 2 um to about 50 um. Optionally, the polymeric coating includes a primer layer disposed on the stent body, a drug-loaded layer disposed on the primer layer, and a topcoat layer disposed on the drug-loaded layer so as to control elution of the drug. Accordingly, the polymeric coating is characterized by at least one of the following: the primer layer being from about 1% to about 20% of the total coating thickness; the drug-loaded layer being from about 25% to about 90% of the total coating thickness; or the topcoat being from about 5% to about 50% of the total coating thickness.

In one embodiment, the stent body is a superelastic alloy such as nitinol. This can be linear superelastic and non-linear superelastic nitinol.

In one embodiment, the drug is a rapamycin analog such as everolimus or zotarolimus.

In one embodiment, the polymer coating and/or polymeric topcoat is an ethylenevinylalcohol copolymer.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
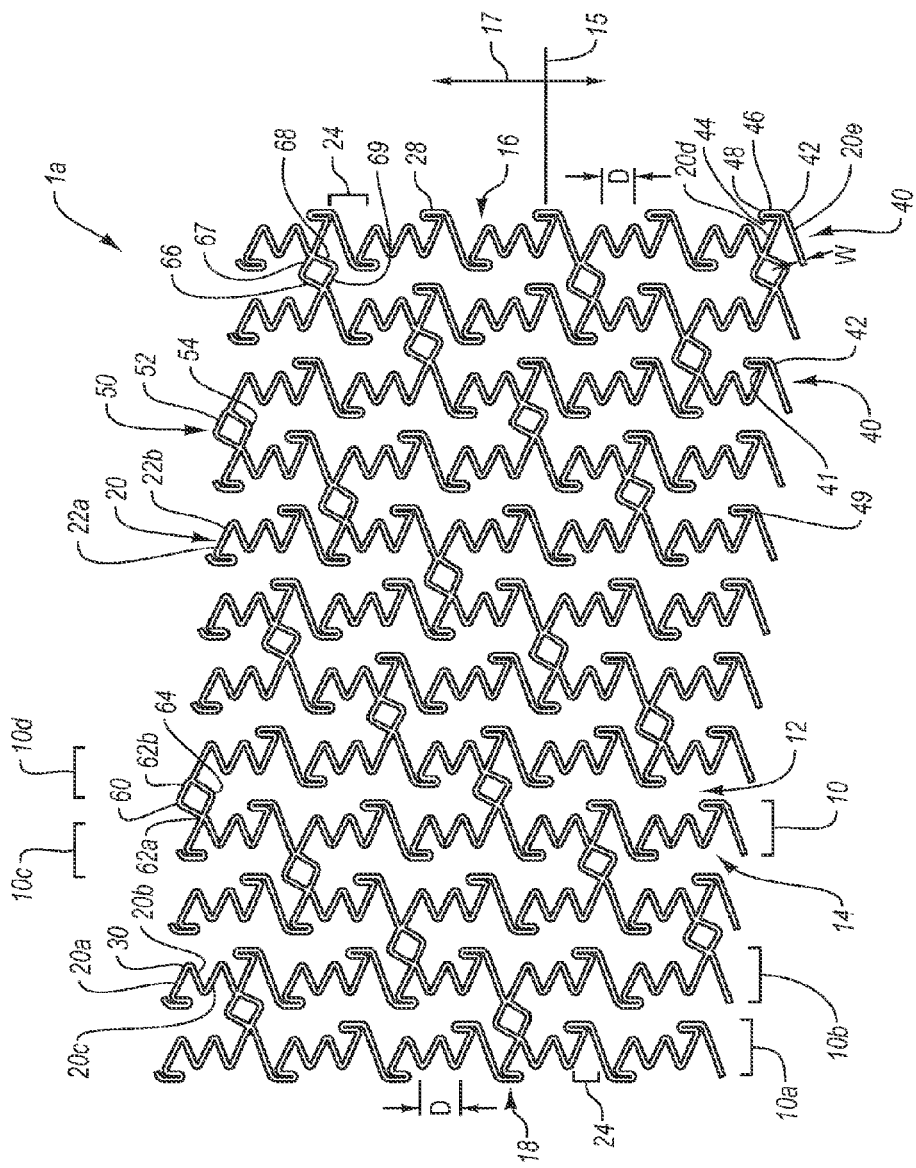
FIG. 1 is a planar side view of a portion of an embodiment of an exemplary endoprosthesis in accordance with the present invention.

Generally, the present invention includes drug eluting implantable medical devices such as endoprostheses, vena cava filters, embolic protection filters, and the like that are configured with controlled drug delivery profiles that allow for enhanced drug delivery into the lumen tissue adjacent to the implantable medical device and that inhibits drug delivery into the systemic blood circulation. The preferential drug delivery into the lumen tissue can be facilitated by a hydrophobic component being included in a coating on the medical device (e.g., stent or vena cava filter) that is in contact with the lumen tissue. The hydrophobic components of the tissue cooperate with the hydrophobic component of the coating so as to facilitate preferential diffusion of a hydrophilic drug into the tissue over into systemic blood. Similarly, the drug can be hydrophilic or amphipathic by having both lipophilic and hydrophilic portions. The polymer can include a hydrophilic component for the hydrophilic drug, and hydrophilic and/or hydrophobic components for the lipophilic, hydrophilic, or amphipathic drugs.

As used herein, the term "micro" has been abbreviated with the standard symbol "μ" or "u" for simplicity.

I. Drug Eluting Endoprosthesis

In accordance with the present invention, a drug eluting endoprosthesis can be provided for improved drug delivery within a body lumen of a human or other animal. Examples of drug eluting endoprostheses can include stents, filters, grafts, valves, occlusive devices, trocars, aneurysm treatment devices, or the like. Additionally, the drug eluting endoprosthesis can be configured for a variety of intraluminal applications, including vascular, coronary, biliary, esophageal, urological, gastrointestinal, or the like.

Additional medical device embodiments, i.e. vena cava filter that can be implanted in the vena cava to elute drug over time. The device becomes a systemic drug release device instead of a device to treat an area of stenosis. The drug release device could replace daily pills for individuals in need of the therapy provided by the drug, such as transplant patients.

Generally, an endoprosthesis of the present invention can include at least a first set of interconnected strut elements that cooperatively define an annular element. A strut element can be more generally described as an endoprosthetic element, wherein all well-known endoprosthetic elements can be referred to here as a "strut element" for simplicity. Usually, each strut element can be defined by a cross-sectional profile as having a width and a thickness, and including a first end and a second end bounding a length. The stent element can be substantially linear, arced, rounded, squared, combinations thereof, or other configurations. The strut element can include a bumper, crossbar, connector, interconnector, intersection, elbow, foot, ankle, toe, heel, medial segment, lateral segment, coupling, sleeve, combinations thereof, or the like, as described in more detail below. The strut element can have improved structural integrity by including crack-inhibiting features, which are described in detail in the incorporated references.

Usually, the annular elements can include a plurality of circumferentially-adjacent crossbars that are interconnected end-to-end by an elbow connection, intersection, or a foot extension. As such, at least one annular element or endoprosthesis can include an elbow, intersection, or a foot extension (foot) extending between at least one pair of circumferentially-adjacent crossbars. The elbow or foot can thus define an apex between the pair of circumferentially-adjacent crossbars of the annular element or endoprosthesis. Also, an intersection can have a shape similar to a crossbar or interlinked crossbars so as to provide a junction between two coupled pairs of circumferentially-adjacent crossbars.

The elbow can be configured in any shape that connects adjacent ends of circumferentially-adjacent crossbars, and can be described as having a U-shape, V-shape, L-shape, X-shape, Y-shape, H-shape, K-shape, or the like. The elbow and/or intersection can be configured in any shape that connects longitudinal and circumferentially adjacent crossbars, and can be described as having a cross shape, X-shape, Y-shape, H-shape, K-shape, or the like. The foot can have a foot shape having a first foot portion extending circumferentially from an end of one of the adjacent strut members and a second foot portion extending circumferentially from a corresponding end of the other of the circumferentially-adjacent strut members. In combination, the first and second foot portions generally define an ankle portion connected to a toe portion through a medial segment and the toe portion connected to a heel portion through a lateral segment.

As described herein, an endoprosthesis, in one configuration, can include two or more interconnected annular elements. Each annular element can generally define a ring-like structure extending circumferentially about a longitudinal or central axis. The cross-sectional profile of each annular element can be at least arcuate, circular, helical, or spiral, although alternative cross-sectional profiles, such as oval, oblong, rectilinear or the like, can be used. The different annular elements can be defined as having the same characterization or different characterizations.

The first and second annular elements generally define a tubular structure. For example, each annular element can define a continuous closed ring such that the longitudinally-aligned annular elements form a closed tubular structure having a central longitudinal axis. Alternatively, each annular element can define an open ring shape such that a rolled sheet, open tubular, or "C-shape" type structure is defined by the annular elements. That is, the annular element is not required to be closed. Furthermore, each annular element can define substantially a 360-degree turn of a helical pattern or spiral, such that the end of one annular element or endoprosthesis can be joined with the corresponding end of a longitudinally-adjacent annular element or endoprosthesis to define a continuous helical pattern along the length of the endoprosthesis.

FIG. 1 is a side view of a flattened portion of an embodiment of an endoprosthesis 1a. The illustrated endoprosthesis is a stent, but it will be understood that the benefits and features of the present invention are also applicable to other types of endoprosthesis or other medical devices known to those skilled in the art.

For purposes of clarity and not limitation, the endoprosthesis Ia is illustrated in a planar format. As shown, the endoprosthesis Ia can include a plurality of annular elements 10 aligned longitudinally adjacent to each other along a longitudinal axis 15 extending from a first end 16 to a second end 18. Although only two interconnected annular elements need to be provided for the endoprosthesis, it is possible that an endoprosthesis include one or a plurality of annular elements 10. As depicted in FIG. 1, at least a first annular element 10a and a second annular element 10b are identified.

Each annular element 10 can include a set of interconnected strut elements, shown as strut crossbars 20, which are disposed circumferentially about the longitudinal axis 15; the circumferential direction is represented by arrow 17. Each crossbar 20 can have a first end 22a and a second end 22b, referenced generally as end 22. The first end 22a of selected circumferentially-adjacent crossbars 20a-b can be interconnected at elbows 30 that are proximate to a first longitudinal side 12 of each annular element 10, and the second end 22b of selected circumferentially-adjacent crossbars 20b-c can be interconnected to define elbows 30 that are proximate to a second longitudinal side 14 of the annular element.

Each annular element 10 can be expanded to a deployed configuration as shown in FIG. 1 by altering or opening the angle of the elbows 30 interconnecting the circumferentially-adjacent crossbars 20, or can be collapsed into a deployable configuration by closing the angle of the elbows 30. Also, circumferentially-adjacent elbows 30 on each side 12, 14 of the annular element 10 can be spaced apart by a circumferential distance D, such that each annular element 10 is expanded by increasing the distance D and collapsed by decreasing the distance D. At any given condition between the delivery configuration and the deployed configuration, the distance D can be balanced or constant from one set of circumferentially-adjacent elbows to the next, or it can be varied if desired.

Selected elbows 30 on each side 12, 14 of the annular element 10 can be defined by interconnecting corresponding ends 22 of circumferentially-adjacent crossbars 20a-b directly together to form a zigzag pattern of alternating U-shapes, V-shapes, L-shapes, combinations thereof, or the like when deployed. Alternatively, an elbow 30 can be provided between the corresponding ends of adjacent crossbars to form another contoured shape, such as by using a straight elbow member to form a flat connection configuration.

FIG. 1 also depicts an embodiment of a foot extension 40 that can extend between a pair 24 of circumferentially-adjacent crossbars 20d-e of each annular element 10. As depicted, the foot extension 40 can include an ankle 41 that circumferentially couples an end 22 of one of the adjacent crossbars 20d to a medial segment 44. The medial segment 44 extends from the ankle 41 to a toe 48 that circumferentially couples the medial segment to a lateral segment 46. The lateral segment 46 can extend from the toe 48 to a heel 42 that circumferentially couples the lateral segment to the next circumferentially-adjacent crossbar 20e. Accordingly, the juncture of the crossbar 20d and the medial segment 44 can define a circumferentially-extending toe portion 48 of the foot extension 40; the juncture of the medial segment 44 and the lateral segment 46 defines a circumferentially-extending toe portion 48 of the foot extension 40; and the juncture of the lateral segment 46 and crossbar 20e defines a circumferentially-extending toe portion 48 of the foot extension 40. Each portion of the foot extension 40, as well as each of the circumferentially-adjacent crossbars 20, can have a substantially uniform cross-sectional profile illustrated by a substantially uniform width W and thickness (not shown).

For purposes of discussion and not limitation, FIG. 1 shows that a toe portion 48 can extend in a first circumferential direction a distance greater than the distance the heel portion 42 of the foot extension 40 extends in an opposite circumferential direction. As such, the entirety of the foot extension 40 can extend in the circumferential direction of the toe portion 48. Furthermore, at least one of the medial segment 44 or lateral segment 46 can open foot region 49.

The adjacent annular elements 10a-10b or 10c-10d can be interconnected with an interconnector 50 as described herein. For example, the interconnector 50 can have a form of a means for reducing force transmission between adjacent annular elements. Stated another way, the interconnector 50, optionally referred to as a force absorber or force absorbing connector, can include one or more force absorbing members that allow limited movement of adjacent annular elements, while reducing the possibility of cracking and fatigue failure due to the movement of adjacent annular elements. As such, the endoprosthesis Ia can include a plurality of interconnectors 50 to connect adjacent annular elements 10a-10b or 10c-10d. Each interconnector 50 can include a first bending member or shock 52 and a second bending member or shock 54, which can bend toward each other to separate the adjacent annular elements 10a-10b or 10c-10d or bend away from each other to being adjacent annular elements closer together. Accordingly, the interconnector 50 can include a first bending point 60 opposite of a second bending point 64. The first bending member or shock 52 can have at least a first arm 66 and a second arm 67. The second bending member or shock 54 can have at least a first arm 68 and a second arm 69. The interconnector 50 can couple with a first crossbar 20 of a first annular element 10c at a first coupling 62a, and couple with a second crossbar of a second annular element 10d at a second coupling 62b.

The endoprosthesis Ia can be easily deployed because of the improved flexibility provided within each annular element 10 or between adjacent annular elements 10a-10b. As such, the resiliently-flexible bending members or shocks 52, 54 can cooperate so as to enable the endoprosthesis Ia to bend around a tight corner by the bending members or force-absorbing members on one side of the annular element contracting while bending members or force-absorbing members on an opposite side expanding. Also, the combination of elbows 30, foot extensions 40, and/or resiliently flexible interconnectors 50 can allow for radial, longitudinal, torsional, or bending loading to be absorbed without cracking, fracturing or damage occurring to the endoprosthesis 1a. Moreover, the resiliently-flexible interconnectors 50 can allow adjacent annular elements to move independently with respect to each other in radial, longitudinal, and cross directions.

While FIG. 1 illustrates one type of endoprosthesis, the general teachings thereof can be applied to other types of endoprostheses. This includes other types of stents that have different strut elements in different shapes and configurations. As such, FIG. 1 is provided as an example of one type of endoprosthesis that can be coated with the polymer/drug of the present invention in order to achieve preferential drug delivery into lumen tissue adjacent to the endoprosthesis.

In one embodiment, the present invention can include a drug eluting stent that has a stent body, a polymeric coating, and a lipophilic drug. The polymeric coating can have a lipophilic element and be disposed on the stent body. The lipophilic drug can have a bioactivity that inhibits cell proliferation, and can be disposed in the polymeric coating. However, any lipophilic drug with any activity can be used for the treatment of an appropriate condition.

In one embodiment, the present invention can include a drug eluting stent that has a stent body, a polymeric coating, and a hydrophilic drug. The polymeric coating can have a hydrophilic element and be disposed on the stent body. For example, the hydrophilic drug can have a bioactivity that inhibits cell proliferation, and can be disposed in the polymeric coating. However, any hydrophilic drug with any activity can be used for the treatment of an appropriate condition.

In one embodiment, the present invention can include a drug eluting stent that has a stent body, a polymeric coating, and an amphipathic drug having both hydrophilic and lipophilic components. The polymeric coating can have a hydrophilic and/or hydrophilic element and be disposed on the stent body. For example, the amphipathic drug can have a bioactivity that inhibits cell proliferation, and can be disposed in the polymeric coating. However, any amphipathic drug with any activity can be used for the treatment of an appropriate condition.

The drug can be present in the polymer at an amount from about 10 μg/cm² (micrograms drug/area of stent) to about 2000 μg/cm², more preferably from about 100 μg/cm² to about 1000 μg/cm², and most preferably from about 200 μg/cm² to about 500 μg/cm². In exemplary stents, the drug per area can include 150 μg/cm² to about 500 μg/cm², more preferably from about 175 μg/cm² to about 400 μg/cm², and most preferably from about 200 μg/cm² to about 300 μg/cm². Within this narrower range, the drug per area can include 210 μg/cm² to about 275 μg/cm², more preferably from about 215 μg/cm², to about 250 μg/cm², and most preferably 225 μg/cm²±10 μg/cm².

In one embodiment, the amount of drug on the stent can be described as the total amount of drug per stent. Accordingly, the amount of drug per stent can be from about 0.5 mg to about 12 mg, more preferably from about 0.75 mg to about 10 mg, and most preferably from about 1 mg to about 5 mg.

In one embodiment, the amount of drug on the stent can be described as the total amount of drug for a stent of a specific length. The amount of drug per stent can be from about 0.5 mg to about 12 mg for stents ranging from about 10 mm to about 300 mm, and more preferably from about 20 mm to about 150 mm stent lengths. This includes about 0.5 mg to about 5 mg, more preferably from about 0.75 mg to about 2.5 mg, and most preferably about 1 mg for a stent having a length from about 10 mm to about 30 mm, more preferably from about 15 mm to about 25 mm, and most preferably about 20 mm. This also includes about 2 mg to about 6 mg, more preferably about 3 mg to about 5 mg, and most preferably from about 3.5 mg to about 4 mg or about 3.8 mg for a stent having a length from about 60 mm to about 100 mm, more preferably from about 70 mm to about 90 mm, and most preferably about 80 mm. Additionally, this can include about 4 mg to about 8 mg, more preferably from about 5 mg to about 7 mg, and most preferably about 6 mg for a stent having a length from about 130 mm to about 170 mm, more preferably from about 140 mm to about 160 mm, and most preferably about 150 mm.

The polymeric coating and drug are configured to cooperate so as to form a diffusion pathway (e.g., lipophilic, hydrophilic and/or amphipathic) with tissue when the stent is disposed in a body lumen such that the drug preferentially diffuses into the tissue over a body fluid passing through the body lumen such that a maximum systemic blood concentration of the drug is less than or about 30 ng/ml, more preferably less than or about 20 ng/ml, and most preferably less than or about 10 ng/ml.

In one embodiment, the polymeric coating can control the systemic delivery of the drug so as to retain a sufficiently low concentration in order to inhibit negative systemic side effects. This can include a 100 mm stent having about 3.8 mg drug eluting the drug so as to obtain a blood maximum concentration (i.e., Cmax) from about 0.6 ng/ml to about 15 ng/ml, more preferably from about 1 ng/ml to about 10 ng/ml, even more preferably from about 2 ng/ml to about 5 ng/ml, and most preferably about 3 ng/ml. This can also include a 200 mm stent having about 7.5 mg drug eluting the drug so as to obtain a blood Cmax from about 1.5 ng/ml to about 30 ng/ml, more preferably from about 3 ng/ml to about 15 ng/ml, even more preferably from about 5 ng/ml to about 10 ng/ml, and most preferably about 6 ng/ml. Additionally, this can include a 300 mm stent having about 12 mg drug eluting the drug so as to obtain a blood Cmax from about 2 ng/ml to about 40 ng/ml, more preferably from about 4 ng/ml to about 30 ng/ml, even more preferably from about 6 ng/ml to about 20 ng/ml, and most preferably about 9 ng/ml.

In one embodiment, the systemic delivery of the drug can be characterized as concentration of drug per length of stent. As such, the systemic delivery of the drug can provide a blood maximum concentration that can be from about 0.6 pg/ml per millimeter (mm) of stent (e.g., 0.6 pg drug per ml of blood per mm of stent) to about 15 pg/ml per mm of stent, more preferably from about 1 pg/ml per mm of stent to about 10 pg/ml per mm of stent, even more preferably about 2 pg/ml per mm of stent to about 5 pg/ml per mm of stent, and most preferably about 3 pg/ml per mm of stent.

In one embodiment, the systemic delivery of the drug can be characterized as concentration of drug per amount of total amount of drug on the stent. As such, the systemic delivery of the drug provide a blood maximum concentration can be from about 0.16 ng/ml per milligram (mg) of drug on the stent to about 4 ng/ml per mg total drug, more preferably from about 0.2 ng/ml per mg total drug to about 3.3 ng/ml per mg total drug, even more preferably about 0.5 ng/ml per mg total drug to about 2.5 ng/ml per mg total drug, and most preferably about 0.75 ng/ml per mg total drug to about 0.8 ng/ml per mg total drug.

In one embodiment, the stent body is comprised of a superelastic alloy, such as nitinol. The nitinol can have an ethylenevinylalcohol copolymer coating disposed thereon. A therapeutically effective amount of everolimus can be disposed in the polymeric coating so as to be present at an amount greater than or equal to about 150 µg/cm$^2$. The polymer coating and everolimus are configured so as to cooperate to form a lipophilic diffusion pathway with tissue when the stent is disposed in a body lumen such that the everolimus preferentially diffuses into the tissue over a body fluid passing through the body lumen and such that a maximum systemic blood concentration of everolimus is less than about 10 ng/ml. In one aspect, the drug can present in an amount greater than or equal to about 200 µg/cm$^2$ and the maximum systemic blood concentration of the drug can be less than about 5 ng/ml. This can also be similar for hydrophilic and amphipathic drugs.

In one embodiment, the drug eluting stent produces a systemic blood concentration of the drug that in turn produces at least one of the following: a maximum kidney concentration of less than or about 50 ng/g, more preferably less than or about 40 ng/g, and most preferably less than or about 30 ng/g; a maximum lung concentration of less than or about 45 ng/g, more preferably less than or about 35 ng/g, and most preferably less than or about 25 ng/g; a maximum muscle concentration of less than or about 35 ng/g, less than or about 30 ng/g, and most preferably less than or about 25 ng/g; a maximum liver concentration of less than or about 30 ng/g, more preferably less than or about 25 ng/g, and most preferably less than or about 17 ng/g; or a maximum spleen concentration of less than or about 35 ng/g, more preferably less than or about 30 ng/g, and most preferably less than or about 25 ng/g.

In one embodiment, the stent can be characterized by one of the following: the drug is present at greater than or about 1070 µg on the stent body that is about 10×28 mm so as to produce a maximum blood concentration of less than or about 3 ng/ml and a maximum lumen tissue concentration of greater than or about 5000 ng/g; the drug is present at greater than or about 1070 µg on the stent body that is about 8×28 mm so as to produce a maximum blood concentration of less than or about 3 ng/ml and a maximum lumen tissue concentration of greater than or about 8000 ng/g; the drug is present at greater than or about 3209 µg on the stent body that is about 8×28 mm so as to produce a maximum blood concentration of less than or about 5 ng/ml and a maximum lumen tissue concentration of greater than or about 20000 ng/g; or the drug is present at greater than or about 3777 µg on the stent body that is about 7×100 mm so as to produce a maximum blood concentration of less than or about 10 ng/ml and a maximum lumen tissue concentration of greater than or about 15000 ng/g.

II. Endoprosthesis Compositions

The drug eluting endoprostheses of the present invention can be made of a variety of materials, such as, but not limited to, those materials which are well known in the art of endoprosthesis (e.g., stent) manufacturing. This can include, but is not limited to, an endoprosthesis body having a primary material. Alternatively, at least two of the annular elements or different portions can be made of different materials. Generally, the materials for the endoprosthesis can be selected according to the structural performance and biological characteristics that are desired.

In one configuration, the endoprosthesis body has multiple layers, with at least one layer being applied to a primary material forming the annular elements. As such, at least one annular element can have multiple layers that are different from at least one other annular element. The multiple layers can be resiliently flexible materials or rigid and inflexible materials, and selected combinations thereof. For example, materials such as Ti3Al2.5V, Ti6Al4V, 3-2.5Ti, 6-4Ti and platinum may be particularly good choices for adhering to a flexible material, such as, but not limited to, nitinol and providing good crack arresting properties. The use of resiliently flexible materials can provide force-absorbing characteristics to the structures, interconnectors, and/or other endoprosthesis components, which can also be beneficial for absorbing stress and strains, which may inhibit crack formation at high stress zones. Also, the multiple layers can be useful for applying radiopaque materials to selected annular elements, such as end annular elements to provide different characteristics. For example, types of materials that are used to make an endoprosthesis can be selected so that the endoprosthesis is capable of being collapsed during placement and expanded when deployed. Usually, the endoprosthesis can be self-expanding, balloon-expandable, or can use some other well-known configuration for deployment. For purposes of illustration and not limitation, reference is made generally to self-expanding embodiments and balloon-expandable embodiments of the endoprosthesis of the present invention; however, other types of endoprostheses can be configured in accordance with the present invention.

Embodiments of the endoprosthesis body can include a material made from any of a variety of known suitable materials, such as a shaped memory material (SMM). For example, the SMM can be shaped in a manner that allows for restriction to induce a substantially tubular, linear orientation while within a delivery shaft, but can automatically retain the memory shape of the endoprosthesis once extended from the delivery shaft. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) comprised of metal alloys, or shape memory plastics (SMP) comprised of polymers. The materials can also be referred to as being superelastic.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. The main types of SMAs are as follows: copper-zinc-aluminum; copper-aluminum-nickel; nickel titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture.

For example, the primary material of an endoprosthesis can be of a NiTi alloy that forms superelastic nitinol. In the present case, nitinol materials can be trained to remember a certain shape, straightened in a shaft, catheter, or other tube, and then released from the catheter or tube to return to its trained shape. Also, additional materials can be added to the nitinol depending on the desired characteristic. The alloy may be utilized having linear elastic properties or non-linear elastic properties.

An SMP is a shape-shifting plastic that can be fashioned into an endoprosthesis in accordance with the present invention. Also, it can be beneficial to include at least one layer of an SMA and at least one layer of an SMP to form a multilayered body; however, any appropriate combination of materials can be used to form a multilayered endoprosthesis. When an SMP encounters a temperature above the lowest melting point of the individual polymers, the blend makes a transition to a rubbery state. The elastic modulus can change more than two orders of magnitude across the transition temperature (Ttr). As such, an SMP can be formed into a desired shape of an endoprosthesis by heating it above the Ttr, fixing the SMP into the new shape, and cooling the material below Ttr. The SMP can then be arranged into a temporary shape by force, and then resume the memory shape once the force has been applied. Examples of SMPs include, but are not limited to, biodegradable polymers, such as oligo($\epsilon$-caprolactone)diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

An endoprosthesis body having at least one layer made of an SMM or suitable superelastic material and other suitable layers can be compressed or restrained in its delivery configuration within a delivery device using a sheath or similar restraint, and then deployed to its desired configuration at a deployment site by removal of the restraint as is known in the art. An endoprosthesis body made of a thermally-sensitive material can be deployed by exposure of the endoprosthesis to a sufficient temperature to facilitate expansion as is known in the art.

Also, the endoprosthesis body can be comprised of a variety of known suitable deformable materials, including stainless steel, silver, platinum, tantalum, palladium, nickel, titanium, nitinol, nitinol having tertiary materials (U.S. 2005/0038500, which is incorporated herein by specific reference), niobium-tantalum alloy optionally doped with a tertiary material (U.S. 2004/0158309, 2007/0276488, and U.S. Ser. No. 12/070,646, which are each incorporated herein by specific reference) cobalt-chromium alloys, or other known biocompatible materials. Such biocompatible materials can include a suitable biocompatible polymer in addition to or in place of a suitable metal. The polymeric endoprosthesis can include biodegradable or bioabsorbable materials, which can be either plastically deformable or capable of being set in the deployed configuration. If plastically deformable, the material can be selected to allow the endoprosthesis to be expanded in a similar manner using an expandable member so as to have sufficient radial strength and scaffolding and also to minimize recoil once expanded. If the polymer is to be set in the deployed configuration, the expandable member can be provided with a heat source or infusion ports to provide the required catalyst to set or cure the polymer.

In one embodiment, the stent or other medical device is made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol stent comparable to that of a stainless steel stent of the same size and strut pattern coated with a thin layer of gold. The nitinol stent has improved radiopacity yet retains its superelastic and shape memory behavior and further maintains a thin strut/wall thickness for high flexibility. For example, the stent according to the present invention has 42.8 atomic percent nickel, 49.7 atomic percent titanium, and 7.5 atomic percent platinum.

In one embodiment, the implant can be made at least in part of a high strength, low modulus metal alloy comprising Niobium, Tantalum, and at least one element selected from the group consisting of Zirconium, Tungsten, and Molybdenum. The medical devices according to the present invention provide superior characteristics with regard to bio-compatibility, radio-opacity and MRI compatibility.

Furthermore, the endoprosthesis body can be formed from a ceramic material. In one aspect, the ceramic can be a biocompatible ceramic which optionally can be porous. Examples of suitable ceramic materials include hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. Optionally, the ceramic can be provided as sinterable particles that are sintered into the shape of an endoprosthesis or layer thereof.

Moreover, the endoprosthesis body can include a radiopaque material to increase visibility during placement. Optionally, the radiopaque material can be a layer or coating any portion of the endoprosthesis. The radiopaque materials can be platinum, tungsten, silver, stainless steel, gold, tantalum, bismuth, barium sulfate, or a similar material.

It is further contemplated that the external surface and/or internal surface of the endoprosthesis body (e.g., exterior and luminal surfaces) as well as the entire body can be coated with another material having a composition different from the primary endoprosthetic material. The use of a different material to coat the surfaces can be beneficial for imparting additional properties to the endoprosthesis, such as providing radiopaque characteristics, drug-reservoirs, and improved biocompatibility.

In one embodiment, at least one biocompatible polymeric layer can be a coating that is applied over the entire endoprosthesis body, or to select portions. Examples of such biocompatible polymeric materials can include a suitable hydrogel, hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyan hydrides, polyanhydride-co-imides, polyesters, polyorthoesters, polycaprolactones, polyesters, polyanhydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL™), propylenevinylalcohol copolymers, polyvinylpyrrolidone (PVP), combinations thereof, polymers having monomers thereof, or the like. Additionally, the coating can include hydrophilic and/or hydrophobic compounds, polypeptides, proteins, amino acids, polyethylene glycols, parylene™, heparin, phosphorylcholine, or the like.

The coatings can also be provided on the endoprosthesis to facilitate the loading or delivery of beneficial agents or drugs, such as therapeutic agents, pharmaceuticals and radiation therapies. As such, the endoprosthetic material and/or holes can be filled and/or coated with a biodegradable material.

Accordingly, the polymeric coating material can contain a drug or beneficial agent to improve the use of the endoprosthesis. Such drugs or beneficial agents can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligonucleotides, cell permeation enhancers, and combinations thereof. Another example of a suitable beneficial agent is described in U.S. Pat. Nos. 6,015,815 and 6,329,386 entitled "Tetrazole-containing rapamycin analogs with shortened half-lives", the entireties of which are herein incorporated by reference.

In addition to various medical devices, the coatings on these devices may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b$/$III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors. Also, it should be recognized that many active agents have multiple pharmaceutical uses other than those specifically recited.

In one configuration, the external surfaces of an endoprosthesis can include a coating comprised of polytetrafluoroethylene (PTFE), expanded PTFE (ePTFE), Dacron, woven materials, cut filaments, porous membranes, harvested vessels and/or arteries, or others such materials to form a stent graft prosthesis. Similarly, a medical device, such as a valve, a flow regulator or monitor device, can be used with the endoprosthesis, such that the endoprosthesis functions as an anchor for the medical device within the body lumen.

In one configuration, different external surfaces of an endoprosthesis, such as a low stress zone less susceptible to flexing, can be coated with functional layers of an imaging compound or radiopaque material. The radiopaque material can be applied as a layer at low stress zones of the endoprosthesis. Also, the radiopaque material can be encapsulated within a biocompatible or biodegradable polymer and used as a coating. For example, the suitable radiopaque material can be palladium platinum, tungsten, silver, stainless steel, gold, tantalum, bismuth, barium sulfate, or a similar material. The radiopaque material can be applied as layers on selected surfaces of the endoprosthesis using any of a variety of well-known techniques, including cladding, bonding, adhesion, fusion, deposition or the like.

III. Superelastic Everolimus Eluting Stent with Ethylenevinylalcohol Coating

In one embodiment, the present invention can include a drug eluting stent that is self expanding. The stent can have a structural body that is prepared from a superelastic material that has shape memory, such as nitinol or the like. The structural body can be coated with at least one polymeric coating, such as ethylenevinylalcohol copolymer (i.e., EVAL), that functions as a drug delivery system that controls the release of drug contained therein. The drug contained within the polymer coating can be an anti-restenotic drug (e.g., rapamycin, everolimus, analogs thereof, and the like) or other drug useful for inhibiting cell proliferation within the vascular lumen. The drug can be any drug having a therapeutic benefit for treating and/or preventing a disease or condition. The polymer coating that contains the drug can also be coated by another layer of the same or different polymer that further controls the drug release profile from the stent.

In one embodiment, the stent of the present invention is an everolimus-eluting self-expanding nitinol stent with an elution rate-controlling polymeric coating prepared from ethylenevinylacetate copolymers. The stent was designed to address and overcome three potential shortcomings of prior self-expanding DES, namely (1) inadequate drug delivery to the target tissue, (2) short profiles of elution leading to transiently high systemic drug concentrations, and (3) a tendency towards strut fracture when implanted into the SFA. The design features of the present invention that address these drawbacks are detailed below.

In one embodiment, a coated stent can be loaded with a relatively high overall drug content (e.g., 225 μg everolimus/$cm^2$ stent area) as compared to other coronary stents that elute analogs of everolimus (e.g., 140 μg sirolimus/$cm^2$ or 160 μg zotarolimus/$cm^2$). Everolimus (40-O-(2-hydroxyethyl)-rapamycin; Novartis Pharmaceuticals Corporation, Basel, Switzerland) is a macrolide immunosuppressant analog of rapamycin (i.e., sirolimus) that, in conjunction with cyclosporine, has been shown to be effective in inhibiting chronic rejection episodes of solid organ transplants. Its oral formulation is marketed outside the United States under the trade name Certican®. Everolimus effectively inhibits neointimal hyperplasia in animal models and, when formulated onto coronary stents at a dose of 150 µg everolimus/cm$^2$ stent area, it reduces restenosis as compared to bare metal or paclitaxel-eluting stents. The amount of 225 µg everolimus/cm$^2$ stent area is an exemplary dose for the drug eluting stent embodiment as this dose roughly represents a 2:1 increase in dose/mm$^2$ arterial area as compared to the coronary DES formulation.

In one embodiment, the drug eluting stent in accordance with the present invention, which is referred to herein as "STENT A" is characterized as follows: a structural body made of nitinol or other similar superelastic alloy; having a maximum diameter when expanded of 3 mm to about 20 mm, more preferably from about 3.5 mm to about 15 mm, and most preferably from about 4 mm to about 12 mm; having a minimum inner diameter when in a deployable of 0 um (i.e., touching) to about 1000 um, more preferably from about 0 um to about 500 um, and most preferably from about 0 um to about 200 um; and having a polymeric coating of ethylenevinylalcohol at a thickness of about 2 um to about 50 um, more preferably from about 4 um to about 25 um, even more preferably from about 5 um to about 20 um, and most preferably from about 13 to about 15 um.

Figure 2A:
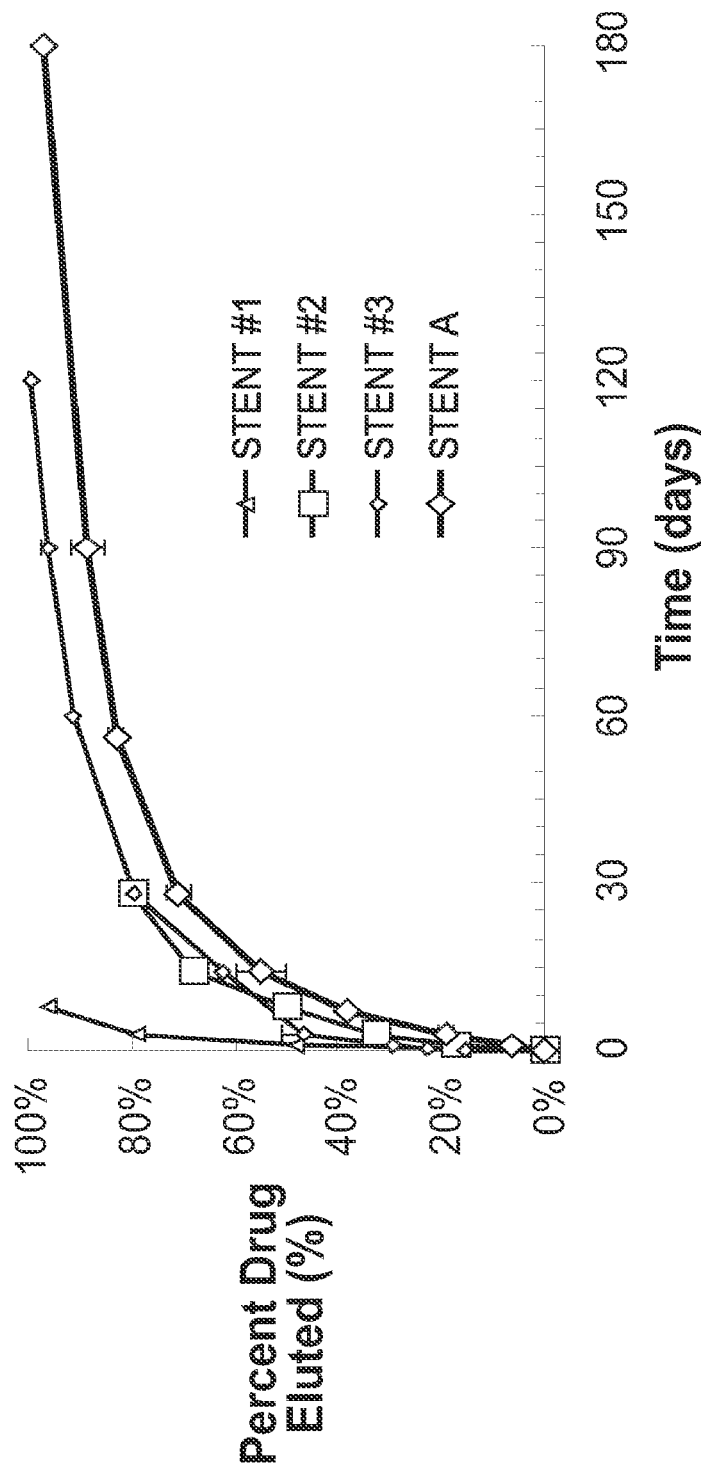
FIG. 2A is a graph illustrating the percent of drug eluted from a drug eluting stent.

Equally important as the total bulk dose of everolimus contained on the stent is its kinetic release profile. Using an EVAL (i.e., ethylene vinyl alcohol) copolymer system, the everolimus eluting stent embodiment was designed to release drug over a longer period of time as compared to coronary stents. In contrast to coronary DES, which release drug over ~30 days, the everolimus eluting stent embodiment can release everolimus more slowly, and thereby eluting approximately 80% of its drug load over the first days 90 days. A comparison of drug release rates for STENT 1, STENT 2, STENT 3, and the everolimus eluting stent embodiment (i.e., stent A) of the present invention is shown in FIG. 2A. The comparatively prolonged everolimus release rate of the stent A embodiment is intended to roughly match the kinetics of nitinol stent expansion. For example, oversized self-expanding nitinol stents continue to enlarge to their nominal diameter and potentially remodel the human arterial wall for at least six months.

Figure 2B:
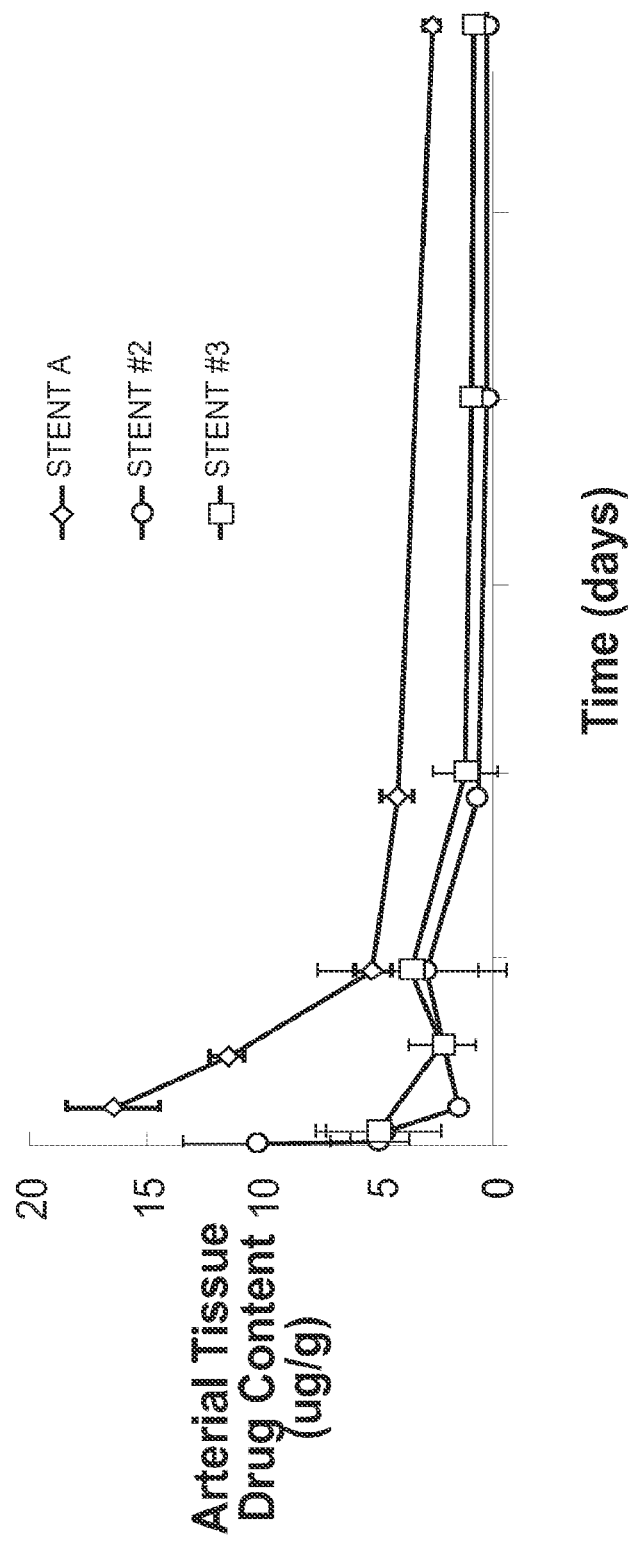
FIG. 2B is a graph illustrating the arterial tissue drug concentration obtained from a drug eluting stent.

The relatively high drug load and slow release profile of the stent A embodiment can assure that the vessel walls of treated peripheral target arteries will contain more everolimus for longer periods of time compared to coronary arteries treated with coronary DES. This is shown in FIG. 2B, which compares porcine arterial drug content for the STENT A embodiment, STENT 2, and STENT 3 treated vessels.

A second salient feature of the slow drug release of the STENT A embodiment is that the potential for systemic everolimus overexposure is minimized. In part, this is because everolimus is released slowly, and thereby the maximum systemic blood concentration of everolimus in stented patients was much lower (e.g., 3-4 ng/ml for a 100 mm stent having about 3.8 mg drug) one hour post-procedure than the recommended upper therapeutic limit in transplanted patients (e.g., 8 ng/ml) and considerably lower than the $C_{max}$ of patients treated with 5 mg everolimus per day in safety studies (e.g., 114 ng/ml).

In one embodiment, the present invention utilizes a well-characterized nitinol stent. As a result, there are ample in vitro and clinical data to suggest that the stent is able to withstand the chronic mechanical forces inherent to the SFA. For example, in a comparative retrospective study of three different peripheral stents, radiographic strut fracture within the nitinol stent was observed in only 1.8% of cases after a mean follow-up of 15±9 months. However, fractures of some nitinol stents were observed in 28% and 19% of cases, respectively (mean follow-up of 32±16 months and 43±24 months, respectively). Similarly, in a randomized, prospective, single-center study of percutaneous transluminal angioplasty (PTA) alone v. PTA with the nitinol stent embodiment, the nitinol stent fracture was observed in only 2% of patients. Finally, in a multicenter single-arm prospective registry, strut fracture of the nitinol stent embodiment was observed in 2.1% (3/143) stents after one year. Taken together, the results of these three studies suggest that the nitinol stent is well-suited to the environment of the SFA, and that chronic implantation is not associated with high rates of fracture. A nitinol stent can be configured to include a polymer having a drug so as to be a drug eluting stent in accordance with the present invention.

In one embodiment, the present invention includes an everolimus-eluting, self-expanding nitinol stent. Such a stent can be used to inhibit restenosis after endovascular intervention in the SFA by selectively eluting everolimus into the vasculature tissue in an amount significantly higher than systemic elution into the bloodstream. As provided herein, there is ample in vitro, in vivo, experimental, and clinical evidence to suggest that the everolimus-eluting, self-expanding nitinol stent (1) delivers a relatively high concentration of everolimus to the target vascular tissue over a prolonged therapeutic interval, (2) minimizes potential systemic exposure to everolimus through a slow systemic (e.g., blood) release profile, and (3) can withstand and adapt to the rigorous mechanical environment of the SFA.

In one embodiment, the present invention provides a drug-eluting stent having a prolonged elution profile with high local concentration and low systemic concentration. The stent can include any stent body that is balloon or self expandable. The stent body includes a first coating layer disposed therein, which includes a mixture of polymer and drug. The first coating layer includes a second coating layer of polymer disposed thereon. The first coating layer can be configured to allow the everolimus to be controllably released from the stent. The second coating layer can, optionally with the first coating layer, control the release of the drug in a manner that prolongs the release profile.

In one aspect, the polymeric coatings can cooperate so as to control elution of the drug from the stent. This can include facilitating elution into the tissue adjacent to the stent and inhibiting elution into the bloodstream, thereby inhibiting systemic drug. The controlled elution can be accomplished by the coatings and artery tissues establishing a diffusion pathway having a steep concentration gradient with respect to the drug so as to induce the drug to diffuse through the diffusion pathway. The steep concentration gradient is accomplished by the coatings having a high concentration of drug and the tissue having a low concentration of drug, which thereby promotes diffusion through the diffusion pathway. Also, the coatings, drug, and tissue can provide lipophilic and/or hydrophilic diffusion pathways with the tissue being a sink to promote diffusion of the drug into the tissue.

Additionally, the diffusion pathway into the vascular tissue can be enhanced by the stent being placed in a blood vessel that passes blood. Blood, while containing some lipid-based components, is significantly more aqueous that than lipidic because the blood includes a significant amount of water. As such, a lipophilic drug will preferentially diffuse through a lipophilic diffusion pathway over an aqueous pathway. The lipophilic drug preferentially diffusing through the lipophilic diffusion pathway into the tissue adjacent to the stent over diffusion into the blood attributes to the vascular tissue adjacent to the stent obtaining a therapeutic concentration of drug and the system concentration being significantly below a therapeutic concentration and toxic concentration. Accordingly, systemic effects of the drug can be inhibited by maintaining an extremely low systemic drug concentration, thereby inhibiting the adverse effects of prolonged systemic drug. This can also be accomplished with hydrophilic and/or amphiphilic drugs and polymer components because tissues inherently have water as a major component.

In one embodiment, the coating/drug combination is configured to provide an extended elution profile that can elute substantially constant levels of drug over 3 months, more preferably over 6 months, and most preferably over 9 months. The slow elution kinetics attribute to the significantly inhibited systemic elution of the drug and helps to maintain the systemic of the drug below any therapeutic and/or toxic index. Additionally, the slow elution kinetics attributes to the drug preferentially diffusing through the lipophilic diffusion pathway because slow elution kinetics further drive the lipophilic drug through a lipophilic diffusion pathway over diffusing into the blood. Also, the slow elution kinetics can enable the tissue to retain sink-like properties with respect to the drug so as to provide a continuously steep concentration gradient through the lipophilic diffusion pathway.

In embodiments of the present invention that include self-expanding stents, the stent continually applies pressure to the vascular tissue. This continual application of pressure can cause the tissue to form troughs that receive the stent elements therein so that the contact area between the tissue and the stent is increased. Also, it is possible that such continuous pressure actually facilitates preferential diffusion of the drug through the lipophilic diffusion pathway. This can occur by the pressure shortening the diffusion pathway between the stent and the tissue by compression of the lipid membranes and/or compression of the coating layers.

It is thought, without being bound thereto, that the coating/drug combination that provides preferential diffusion of the drug through the lipophilic diffusion pathway over diffusion into the systemic blood supply cooperates with natural physiological processes in order to further differentiate the amount of drug in the vascular tissue adjacent to the sent compared to systemic drug. The difference in drug diffusion pathways that result in extremely low systemic concentrations is supplemented by the physiological functions of drug metabolism. Drug metabolism occurs mainly in organs that are removed from the vascular tissue, and preferentially not in the vascular tissue. This physiological process naturally further reduces the systemic concentration of drug without reducing the concentration of drug in the vascular tissue.

In one embodiment, the polymer/drug combination that is configured for prolonged elution can also allow for a substantially greater amount of drug loading on the stent. Previously, drug elution profiles have only allowed for low quantities of drug to be applied to the stent so as to prevent excessively high elution rates and thereby excessively high local and systemic drug concentrations. Some of the previously used stents with low drug loading concentrations have caused higher systemic drug concentrations. Now, the polymer/drug combination of the present invention can allow for substantially increased drug loading on the stent with reduced systemic concentrations. For example, stents that produce excessive systemic concentrations of drug have had relatively lower amounts of drug, such as the following: stent 2 having 140 $\mu g/cm^2$; stent 3 having 100 $\mu g/cm^2$; and stent 1 having 90 $\mu g/cm^2$. However, the polymer/drug combination of the present invention can allow for the stents to have a substantially higher amount of drug loading with lower systemic blood concentrations. For example, the present invention can have a drug loading preferably greater than or equal to about 150 $\mu g/cm^2$, more preferably greater than or equal to about 200 $\mu g/cm^2$, and most preferably greater than or equal to about 225 $\mu g/cm^2$.

Similarly, the stents of the present invention can have substantially more total drug per stent than the stents that produce excessive systemic drug concentrations. For example, stents that produce excessive systemic concentrations of drug have had relatively lower amounts of total drug. However, the polymer/drug combination of the present invention can allow for the stents to have a substantially higher amount of total drug loading. For example, the present invention can have a total drug loading preferably greater than or equal to about 1-3 mg total drug for a short stent, more preferably greater than or equal to about 3-6 mg total drug for a medium length stent, and most preferably greater than or equal to about 6-12 µg total drug for a long stent.

Additionally, the stents of the present invention can have substantially more drug per area of artery into which the drug is to diffuse compared to prior stents. For example, stents that produce excessive systemic concentrations of drug have had relatively lower amounts of drug per area of artery, such as the following: stent 2 having 0.86 to 1.3 $\mu g/mm^2$; stent 3 having 0.49 to 63 $\mu g/mm^2$; and stent 1 having about 0.57 to 0.66 $\mu g/mm^2$. However, the polymer/drug combination of the present invention can allow for the stents to have a substantially higher amount of drug per area of artery. For example, the present invention can have a drug loading preferably greater than or equal to about 1.25 $\mu g/mm^2$ of artery, more preferably greater than or equal to about 1.5 $\mu g/mm^2$ of artery, and most preferably greater than or equal to about 2.0 $\mu g/mm^2$ of artery.

In one embodiment, the polymeric coating can have a thickness of about 2 µm to about 50 µm, more preferably from about 4 µm to about 25 µm, even more preferably from about 5 µm to about 20 µm, and most preferably from about 13 µm to about 15 µm. The coating can be uniform or divided into discrete layers.

In one embodiment, the polymeric coating can having a primer coating against the metal, a drug-loaded coating disposed on the primer coating, and a topcoat disposed on the drug-loaded coating. This can include the primer coating being from about 1% to about 20% of the total coating thickness, more preferably from about 3% to about 15% of the total coating thickness, even more preferably from about 5% to about 10% of the total coating thickness, and most preferably about 7% of the total coating thickness. This can also include the drug-loaded coating being from about 25% to about 90% of the total coating thickness, more preferably from about 40% to about 80% of the total coating thickness, even more preferably about 50% to about 70% of the total coating thickness, and most preferably about 60% of the total coating thickness. Additionally, this includes the topcoat being from about 5% to about 50% of the total coating thickness, more preferably from about 15% to about 40% of the total coating thickness, more preferably from about 25% to about 35% of the total coating thickness, and most preferably about 30% of the total coating thickness.

In one example, a 28 mm stent is coated with 234 µg of primer coating, 3160 µg of drug-loaded coating, and 600 µg of topcoat. The ratio of primer/drug/topcoat layers can be about 1/14/3.

In one embodiment, the prevent invention includes a nitinol stent having a first ethylenevinylalcohol-everolimus coating on the nitinol body and a second ethylenevinyl alcohol coating thereon. In one aspect, the everolimus can be included at 1070 μg for a 10×28 mm stent so as to produce a blood Cmax of less than or about 0.72 ng/ml with a Tmax of 7 days, a tissue Cmax of about greater than or about 6607 ng/g with a Tmax of 3 days, and a half-life ($t_{1/2}$) of about 16.3 days. In another aspect, the everolimus can be included at 1070 μg for a 8×28 mm stent so as to produce a blood Cmax of less than or about 2.29 ng/ml with a Tmax of 1 day, a tissue Cmax of greater than or about 12946 ng/g with a Tmax of 3 days, and a half-life of 11.70 days. In another aspect, the everolimus can be included at 1070 μg for a 8×28 mm stent so as to produce a blood Cmax of less than or about 2.70 ng/ml with a Tmax of 3 days, a tissue Cmax of greater than or about 8709 ng/g with a Tmax of 3 days, and a half-life of 11.51 days. In another aspect, the everolimus can be included at 3209 μg for a 8×28 mm stent so as to produce a blood Cmax of less than or about 3.35 ng/ml with a Tmax of 3 days, a tissue Cmax of greater than or about 22027 ng/g with a Tmax of 3 days, and a half-life of 21.26 days. In another aspect, the everolimus can be included at 3777 μg for a 7×100 mm stent so as to produce a blood Cmax of less than or about 9.6 ng/ml with a Tmax of 0.042 days, a tissue Cmax of greater than or about 16347 ng/g with a Tmax of 3 days, and a half-life of 19.8 days, and which produces a kidney Cmax of less than or about 25.6 ng/g, a lung Cmax of less than or about 22.8 ng/g, a muscle Cmax of less than or about 13.5 ng/g, a liver Cmax of less than or about 15.1 ng/g, and a spleen Cmax of less than or about 23.1 ng/g.

IV. Method of Making Endoprostheses

Various different manufacturing techniques are well known and may be used for fabrication of the drug eluting endoprosthesis of the present invention. Such manufacturing techniques can be employed to make the different annular elements of the drug eluting endoprosthesis. For example, the different annular elements or entire endoprosthesis can be formed from a hollow tube using a known technique, such as laser cutting, EDM, milling, chemical etching, hydro-cutting, and the like. Also, the different annular elements or endoprosthesis can be prepared to include multiple layers or coatings deposited through a cladding process such as vapor deposition, electroplating, spraying, or similar processes. Also, various other processes can be used such as those described below and or others known to those skilled in the art in light of the teaching contained herein.

Optionally, the different annular elements or endoprosthesis can be fabricated from a sheet of suitable material, where the sheet is rolled or bent about a longitudinal axis into the desired tubular shape. Additionally, either before or after being rolled into a tube, the material can be shaped to include endoprosthetic elements by being shaped with well-known techniques such as laser-cutting, milling, etching or the like. If desired, the lateral edges of the structure can be joined together, such as by welding or bonding, to form a closed tubular structure, or the lateral edges can remain unattached to form a coiled, rolled sheet or open tubular structure. Such fabrication techniques are described in more detail below and known to those skilled in the art.

A. Sintering

A method of making different annular elements or endoprosthesis in accordance with the present invention can include sintering sinterable particles to provide a sintered article having the shape of the endoprosthesis. The sintering can be conducted in molds that are in the shape of an endoprosthesis.

In one configuration, the sintered body can be obtained from a molded green body prepared by molding a mixture of sinterable particles with or without a binder into the shape of different annular elements or endoprosthesis or body intermediate. Sintering a molded green body that has the shape of different annular elements or endoprosthesis can provide a sintered body that can function as an endoprosthesis with no or minimal further processing. Alternatively, after the green body has been formed in the mold and sintered into a hardened endoprosthesis, the process can include shaping the sintered body with a stream of energy and/or matter in order to obtain a desired shape. Thus, sintering a green body in a mold can result in an endoprosthesis that is either ready for use, or requires additional processing or finishing.

Additionally, the sintered body can be shaped into an endoprosthesis as described herein. Also, the endoprosthesis can be further processed after sintering and/or shaping such as by grinding, sanding, or the like to provide enhanced surface characteristics.

B. Drawing Concentric Tubes

In one configuration, multilayered annular elements or endoprosthesis in accordance with the present invention can be prepared by a drawing process that draws two or more distinct concentric tubes into a single tube having two or more layers. Additionally, such a drawing process can combine multiple concentric tubes into a single multilayered tube. The drawing process can be configured to produce junctions separating adjacent layers or bonds that bond adjacent layers. As such, the sequentially-adjacent concentric tubes can be drawn together and progressively reduced in a cross-sectional profile until the desired size and residual clamping stress is attained.

Accordingly, a metallurgical bond can be prepared with elements of each sequentially-concentric tube diffusing together and bonding so as to form a strong metallurgical bond. Such a metallurgical bond can be achieved by applying significant pressure and heat to the tubes. As such, a metallurgical bond can form a diffusion layer at the interface between sequentially-adjacent concentric tubes (i.e., layers). The characteristics of these diffusion layers can be controlled by the proper heat treatment cycle. In part, this is because the heat treatment, temperature, and time of processing can control the rates of transfer of the diffusing elements that produce the diffusion layers. Also, the pressure at the interface between layers can be developed so as to result in the residual radial clamping stress in the tube after drawing. A similar process can be used in order to couple the adjacent different annular elements or endoprostheses together to form the hybrid segmented endoprosthesis.

In one example of this process, an outer tube of nitinol, a middle tube of tantalum, and an inner tube of nitinol can be arranged to form the composite structure. The multilayered material can be produced to result in bonding between the layers so as to achieve a residual clamping stress of at least about 50 p.s.i. Accordingly, the annealing process can be performed within a limited range of time and temperatures. For example, the lower limit can be at least about 1550° F. for at least six minutes, and the upper limit can be less than about 1850° F. for less than 15 minutes. A similar process can be used in order to couple the adjacent different annular elements together to form the endoprosthesis.

In another configuration, a metallic interleaf layer can be placed between separate tubes so as to bond the tubes together and form a multilayered material. The multiple tubes separated by the metallic interleaf layer can be drawn together and progressively reduced until the desired cross-sectional profile and residual clamping stress is attained, as described above.

The drawn tubes can be heat-treated to form a diffusion bond between the separate layers. As such, the metallic interleaf layer can enhance the diffusion rate or type of diffusing atoms that are transported across a diffusion region between one layer and the interleaf layer. A similar process can be used in order to couple the adjacent different annular elements together to form the endoprosthesis.

In one configuration, a multilayered sheet can be prepared to have separate layers of different materials or the same material. For example, the multilayered sheet can have a top layer of nitinol, a middle layer of tantalum, and a bottom layer of nitinol. The sheet can be prepared by metallurgically bonding the layers prior to a deep drawing process, which is well known in the art. During the deep drawing process, the sheet can be placed over a die and forced into the die, such as by a punch or the like. A tube having a closed end and a defined wall thickness can be formed in the die. This process can be repeated using a series of dies that have progressively decreasing diameters until a multilayered tube is formed having the desired diameter and wall thickness. For certain material combinations, intermediate heat treatments can be performed between the progressive drawing operations to form a multilayered material that is resistant to delaminating. Once a multilayered tube of desired thickness and dimensions has been formed, the closed end and the curved edges can be cut off. Then, the tube can be heat treated, as described above, until proper inter-metallic bonds are formed between the layers.

C. Shaping

Accordingly, an endoprosthetic material can be shaped by various methods as described in more detail below. Such shaping techniques can utilize streams of energy and/or streams of matter in order to impart shapes into the endoprosthetic material. The streams of energy include photons, electromagnetic radiation, atomic, and sub-atomic materials, as described above. On the other hand, the streams of matter are considered to include materials larger than atomic scale particles, and can be microscopic or macroscopic in size. In any event, the shaping can be designed to direct a stream of energy or a stream of matter at the endoprosthetic material to form an endoprosthetic element and/or holes therein.

In one configuration, a stream of energy can cut, shape, and/or form a tube into an endoprostheses by generating heat at the site where the stream intersects the material, as is well known in the art. The thermal interaction can elevate the local temperature to a point, which can cut, melt, shape, and/or vaporize portions of the endoprosthetic material from the rest of the material.

Accordingly, one configuration of the stream-cutting apparatus can operate and shape the endoprosthetic material by thermal interactions. As such, any of the thermal processes described herein can be used for thermal-cutting. For example, such thermal interactions can arise from laser beam treatment, laser beam machining, electron beam machining, electrical discharge machining, ion beam machining, and plasma beam machining.

In one configuration, by knowing the thermal properties of the endoprosthetic material, precise energy requirements can be calculated so that the thermal beam provides the appropriate or minimum energy for melting and/or vaporizing the material without significantly melting undesirable portions of the material. For example, laser beams are a common form of a stream of energy that can be used to shape the endoprosthetic material. Additionally, there are instances where a laser is preferred over all other cutting techniques because of the nature of the resulting endoprosthesis as well as the characteristics of the endoprosthetic material.

In one configuration, an endoprosthesis may be manufactured as described herein using a femtosecond laser. A femtosecond laser may be desirable in producing an endoprosthesis in accordance with the multilayered composite structure of the present invention because it produces a smaller heat influence zone (HIZ) or heat affected zone (HAZ) compared to other lasers, or it can substantially eliminate the HIZ or HAZ. In comparison, cutting an endoprosthesis using known methods can result in the tubular material being melted away, and thereby forming the pattern in the tubular member. Such melting can result in embrittlement of some materials due to oxygen uptake into the HIZ.

In one configuration, electrical discharge machining is used to shape endoprosthetic material and/or form holes in the endoprosthetic material as desired. As such, electrical discharge machining can be capable of cutting all types of conductive materials such as exotic metal including titanium, hastaloy, kovar, inconel, hard tool steels, carbides, and the like. In electrical discharge, the main interaction between the stream of energy and the endoprosthetic material is thermal, where heat is generated by producing electrical discharges. This can lead to the endoprosthetic material being removed by melting and evaporation. Some examples of electrical discharge machining include wire electron discharge machining, CNC-controlled electrical discharge machining, sinker electrical discharge machining, small hole discharge machining, and the like.

In another configuration, a charged particle beam can be used for shaping the endoprosthetic material, wherein electron beams and ion beams exemplify charged particle beams. A charged particle beam is a group of electrically-charged particles that have approximately the same kinetic energy and move in approximately the same direction. Usually, the kinetic energies are much higher than the thermal energies of similar particles at ordinary temperatures. The high kinetic energy and the directionality of these charged beams can be useful for cutting and shaping of the green bodies, as described herein. Additionally, there are some instances where electron beams or ion beams are preferred over other cutting techniques.

In one configuration, a stream of chemical matter can be used in order to shape or form holes in the endoprosthetic material. Chemical-jet milling, for example, provides selective and controlled material removal by jet and chemical action. As such, the process is similar to water-jet cutting, which is described in more detail below. In any event, chemical-jet milling can be useful for shaping various types of endoprosthetic materials, which provides intricate shaping capabilities.

In another configuration, electrochemical shaping can be based on a controlled electrochemical dissolution process similar to chemical-jet milling an endoprosthetic material. As such, the endoprosthetic material can be attached to an electrical source in order to allow an electrical current to assist in the shaping.

In one configuration, hydro-cutting or water-jet cutting can be used to shape an endoprosthetic material. Hydro-cutting is essentially a water-jet technology that uses the high force and high pressure of a stream of water directed at the endoprosthetic material in order to cut and shape the material as desired. Hydro-cutting can be preferred over some of the other stream-cutting technologies because it can be free of heat, flame, and chemical reactions, and can provide a precise cold shaping technique. Also, heated water with or without being doped with reactive chemicals can also be used. Hydro-cutting is particularly suitable for polymeric endoprostheses, but can be used for metal materials when combined with abrasive particles, as described below.

Additionally, hydro-cutting can be enhanced by the introduction of particulate materials into the water feed line. As such, some hydro-cutting techniques utilize garnet or other rigid and strong materials in order to apply an abrasive cutting force along with the force applied by the water itself. Also, the hydro-cutting process in the present invention can be used with or without inclusion of such abrasives.

Additionally, one of the benefits of hydro-cutting is the ability to reutilize and recycle the spent water-jet material. As such, the endoprosthetic material can be easily separated from the spent water, thereby enabling the recycling and reuse of the water during the hydro-cutting process.

In one configuration, sandblasting, which fits into the regime of stream of matter cutting, can be used to shape an endoprosthetic material by projecting a high energy stream of sand particles at the material. Sandblasting cuts materials in a manner similar to hydro-cutting, especially when the waterjet is doped with abrasive particulates. Additionally, various other particulate streams other than sand can be used in the stream-cutting techniques and machinery.

D. Additional Processing

An additional step of passivation can be performed during the manufacturing stage of the endoprosthesis in order to form a homogeneous oxide layer for corrosion-resistance. The passivation process may be performed prior to installation of the markers in accordance with the present invention or it may be performed after installation of the radiopaque markers. It can also be done before or after the different annular elements or endoprostheses are coupled together. Alternatively, multiple passivation processes may be performed, once prior to application of the markers, and again after insertion of the markers.

As originally shaped and/or fabricated, the annular elements or endoprosthesis can correspond to a delivery configuration, to a deployed configuration, or to a configuration therebetween. The annular elements or endoprosthesis can be fabricated with a configuration at least slightly larger than the delivery configuration. In this manner, the endoprosthesis can be crimped or otherwise compressed into its delivery configuration in a corresponding delivery device.

In another configuration, the annular elements or endoprosthesis can be originally fabricated from a tube having a diameter corresponding to the deployed configuration. In this manner, the longitudinally-free portions of the annular elements (e.g., elbow or foot not at a connection location) and circumferentially-free portions (e.g., the toe and/or heel portion of the foot extensions) can be maintained within the general cylindrical shape (e.g., diameter) of the endoprosthesis when deployed, so as to avoid such portions from extending radially inward when in the deployed configuration. The endoprosthesis can be designed to match the target vessel in which the endoprosthesis is to be deployed. For example, a stent can be provided with an outer diameter in the deployed configuration ranging from about 1 mm for neurological vessels to about 25 mm for the aorta. Similarly, a stent can be provided with a length ranging from about 5 mm to about 200 mm. Variations of these dimensions will be understood in the art based upon the intended application or indication for the endoprosthesis.

Also, the geometry of each component of the endoprosthesis or endoprosthetic element, such as the width, thickness, length and shape of the strut elements, interconnectors, crossbars, connectors, elbows, foot portions, ankle portions, toe portions, heel portions and the like can be selected to obtain predetermined expansion, flexibility, foreshortening, coverage scaffolding, and cross-sectional profile characteristics. For example, longer crossbars and/or connectors can promote greater radial expansion or scaffolding coverage. The phase difference or circumferential alignment between adjacent annular elements likewise can be altered to control coverage and flexibility. Similarly, the number and placement of connection locations and, if present, the connectors, between longitudinally-adjacent annular elements can be selected to obtained the desired flexibility of the endoprosthesis. The number of elbows and/or foot extensions between connection locations also can be varied to achieve desired performance characteristics.

E. Coatings

After the endoprosthesis body is formed, a polymeric coating can be applied thereto. The coating can be applied as is well known in the art of drug eluting stents were polymers are used to retain the drug and allow for diffusion therefrom. Some of the methods for coating endoprostheses (e.g., stents) with polymers include dipping, spraying, inkjetting, painting, brushing, rolling, or otherwise depositing the polymeric coating on the endoprosthesis body. This can include such processes for one or more concentric layers of polymeric coating materials.

In one embodiment, the drug is mixed into a polymeric solution that is applied to the endoprosthesis by an acceptable method of application. Alternatively, a first layer of polymer can be applied to the stent and then a drug layer can be applied thereto with a topcoat of polymer being applied over the drug layer. In another alternative. A coated stent can be dipped into a drug solution so that the drug diffuses into the polymeric coating to achieve the desired amount of drug. In yet another alternative, a bare endoprosthesis can have a layer of drug applied thereto with at least one layer of polymer applied thereto.

After application of a fluid or gelatinous coating, the endoprosthesis can be dried so that the coating can be substantially solidified. Such drying can be accomplished by passive or active drying. Passive drying includes retaining the coated stent in normal or ambient conditions so that a natural drying process occurs. Active drying includes the use of head or forced air to cause the solvent in the liquid coating to evaporate from the coating, and thereby harden the coating so as to be substantially solid.

In one embodiment, the coating or plurality of coatings are applied by a plurality of spray layers. For example, the primer coating can be formed from about 2-3 passes of spraying polymer, the drug-loaded coating can be formed from about 26 passes of spraying polymer, and the topcoat can be formed from about 13 passes of spraying polymer.

V. Method of Delivering Hybrid Segmented Endoprosthesis

Generally, the drug eluting endoprosthesis of the present invention can be delivered into a body of a subject by any method known or developed. For example, the method of using catheters to deploy self-expandable or balloon-expandable stents can be employed.

In one embodiment, the endoprostheses of the present invention are configured for use in a body lumen. As such, the present invention includes a method of delivering the endoprosthesis into a body lumen of a subject. Such a method includes: providing an endoprosthesis as described herein; orienting the endoprosthesis into a delivery orientation with a cross section that is smaller than the body lumen; inserting the endoprosthesis in the delivery orientation into a delivery device, such as a deliver catheter that can be configured substantially as a catheter for delivering a stent; delivering the endoprosthesis to a desired deployment site within the body lumen of the subject; removing the endoprosthesis from the delivery device; and expanding the endoprosthesis so as to have an enlarged dimension that applies radial forces to an inner wall of the body lumen.

Figure 5A:
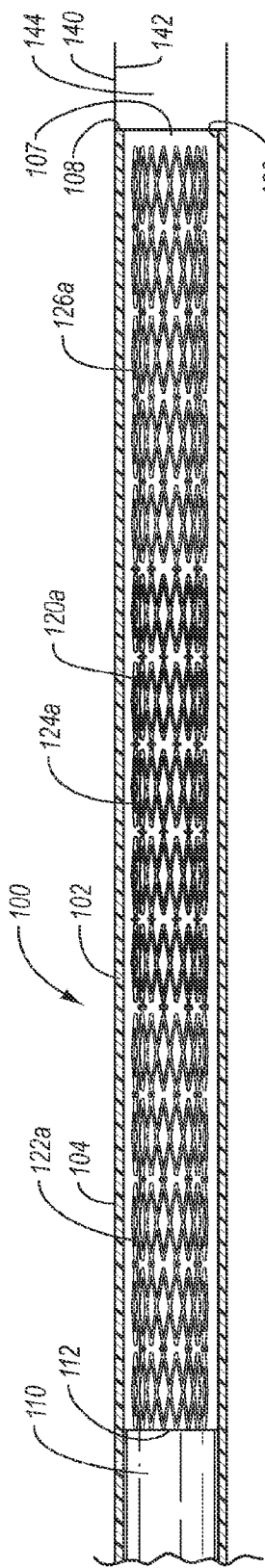
FIGS. 5A-5C include schematic representations of a stent delivery system (FIG. 5A) and a method of delivering the stent into a body lumen (FIG. 5B) with the stent delivery system of FIG. 5A.
Figure 5B:
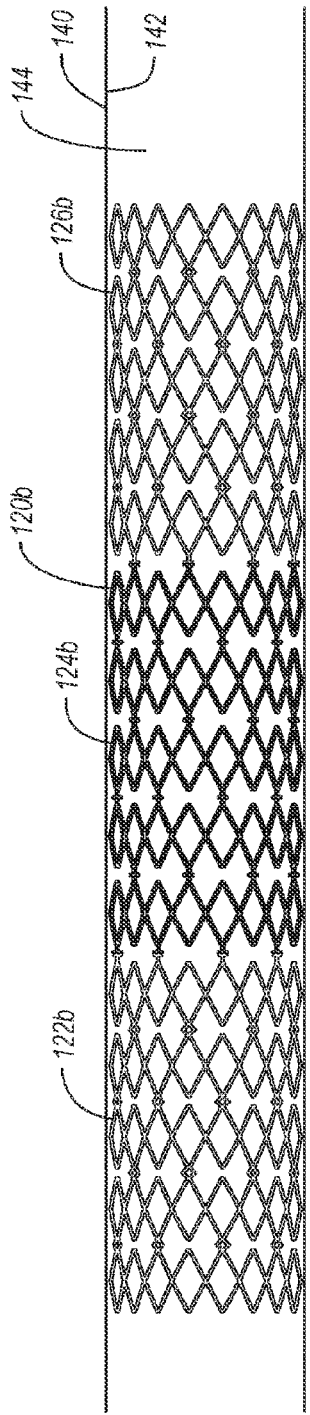
Figure 5C:
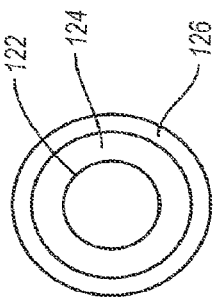

FIGS. 5A-5B are side views illustrating an embodiment of a drug endoprosthesis and methods of deploying such an endoprosthesis into a body lumen in accordance with the present invention. The endoprosthesis 120a is a drug eluting stent, which is depicted in FIG. 5C to show 3 different layers as follows: a stent body layer 124, a polymer/drug coating 122, and a polymeric topcoat 126 that controls drug diffusion from the stent, where 122a, 124a, and 126a designate the delivery configuration and 122b, 124b, and 126b designate the deployed configuration.

FIG. 5A is a schematic representation illustrating a delivery system 100 for delivering a drug eluting endoprosthesis 120a into a body lumen 140, such as a blood vessel like the vena cava. The delivery system includes an endoprosthesis delivery catheter 102 configured for delivering a drug eluting endoprosthesis 120a that is retained by the catheter 102 in a delivery orientation (e.g., radially compressed). The delivery catheter 102 includes a delivery member 104 that defines a delivery lumen 107 that is shaped and dimensioned to retain the endoprosthesis 120a in the delivery orientation. Accordingly, the delivery member 104 is substantially tubular and configured similarly as any delivery catheter member. An internal surface 106 defined by the delivery member 104 holds the endoprosthesis 120a within the delivery catheter 102.

The delivery system 100 delivers the endoprosthesis 120a with a catheter 102 similarly to the method of delivering other endoprostheses into a body lumen. As such, an insertion site (not shown) is formed through the skin (not shown) that traverses into a body lumen 140. A guidewire (not shown) is then inserted through the insertion site, through the body lumen 140, to the delivery site 144. A catheter (not shown) is then inserted into the body lumen 140 to the delivery site 144 over the guidewire, and the guidewire is optionally extracted. The delivery catheter 102 is then inserted through the catheter (not shown) until reaching the delivery site 144 and the catheter is withdrawn.

Optionally, the catheter is the delivery catheter 102, and in this instance, the delivery catheter 102 is retained at the delivery site 144 and the endoprosthesis 120a is delivered to the delivery site 144 through the lumen 107 of the delivery catheter 102. An optional pusher or stop 110, having a lumen (not shown) to receive the guidewire (not shown), can be used to push the endoprosthesis 120a within the lumen 107 of the delivery catheter 102 to the delivery site 144 or limit proximal movement of the endoprosthesis 120a as the delivery catheter 102 is moved proximally to deploy the endoprosthesis 120a.

Accordingly, the delivery system 100 is inserted through percutaneous insertion site (not shown) that traverses from the skin (not shown) into the body lumen 140 until reaching the delivery site 144. The pusher 110 includes a distal end 112 that pushes the endoprosthesis 120a from the distal end 108 of the delivery member 104. Alternatively, the endoprosthesis 120a can be disposed at the distal end 108 of the delivery member 104, and the pusher 110 holds the endoprosthesis 120a at the delivery site 144 and the delivery member 104 is retracted over the endoprosthesis 120a and pusher 110. Thus, the pusher 110 can push the endoprosthesis 120a from the delivery catheter 102 or the delivery member 104 can be withdrawn over the endoprosthesis 120a and pusher 110 in order to deploy the endoprosthesis 120a. Combinations of these are also possible.

FIG. 5B illustrates the endoprosthesis 120b in the deployed configuration at the delivery site 144 within the body lumen 140. As such, the endoprosthesis 120b is radially expanded so as to contact the inner wall 142 of the body lumen 140.

In one embodiment, the present invention can include a method of extracting the endoprosthesis from the body lumen, which can include: inserting an endoprosthesis-extracting medical device into the body lumen so as to come into contact with the endoprosthesis; engaging the endoprosthesis-extracting medical device with the endoprosthesis; radially compressing the endoprosthesis so as to have a reduced dimension with a cross section that is smaller than the body lumen; and retrieving the endoprosthesis from the desired deployment site within the body lumen of the subject. Optionally, the endoprosthesis can be received into the endoprosthesis extracting medical device, which can be substantially similar to a catheter.

In one embodiment, at least one of delivering or retrieving the endoprosthesis is performed with a catheter. Catheters configured for delivering and/or retrieving endoprostheses from a body lumen can be adapted for delivering and/or retrieving the endoprosthesis of the present invention.

VI. Lumen Filter

In one embodiment, the medical device of the present invention having the drug-loaded polymer coating can be a lumen filter, such as a vena cava filter. The drug-loaded polymer coating can provide substantially the same drug elution profile with increased local tissue concentration and decreased blood and systemic concentration as described herein.

In one embodiment, the lumen filter is configured for a use other than filtering clots from the lumen; however, such a function can also be performed. The lumen filter embodiment is configured to deliver the drug loaded in the polymer to the lumen in which the filter is disposed without a substantial amount of systemic delivery. As such, the delivery profile from the lumen filter can be substantially as shown herein.

Figure 6A:
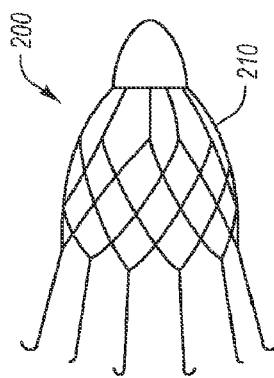
FIGS. 6A-6C include schematic representations of a lumen filter (FIG. 6A) that is deployed into a body lumen with a lumen filter delivery system (FIG. 6B) and a method of delivering the stent into a body lumen (FIG. 6C) with the lumen filter delivery system of FIG. 6B.
Figure 6B:
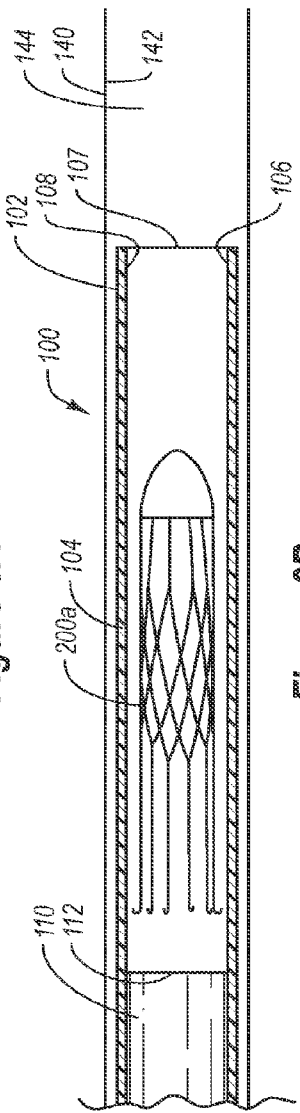
Figure 6C:
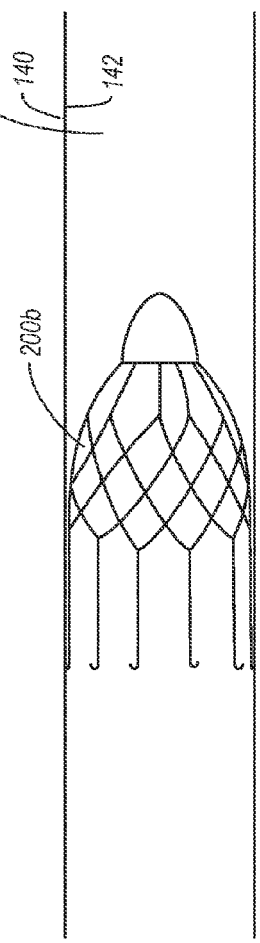

As shown in FIGS. 6A-6C, the lumen filter 200 can include a substantially tubular or conical-shaped body 210, the walls of which can be partitioned by a slot pattern, web, latticework or the like rendering the body radially expandable. Additionally, a plurality of tines can be included in the body 210 in substantially uniform circumferential spacing about the proximal end of said tubular body. In a filter intended for femoral vein introduction into the vena cava the tines can be elongated appendages having hooked terminal ends. In a filter intended for jugular vein introduction the tines can be short spikes. The filter can be delivered to the inferior vena cava by catheters as is well known in the art, including through the technique and structures discussed above with respect to endoprosthesis 120a.

The filter can be delivered substantially as described in for the endoprosthesis 120a in FIGS. 5A-5B, and the elements thereof are include in FIGS. 6B-6C. For example, after the proper location is obtained within the body lumen, i.e., the delivery site 144 of FIG. 6B is attained, the filter 200 can be deployed from the distal end of the catheter 102 through distal movement of the pusher 110, proximal movement of catheter 102, or a combination of distal and proximal movements. With the filter 200 being self-expanding, releasing the filter 200 from the distal end of the delivery catheter 102 allows the filter 200 to expand into the body lumen affix the expanded filter 200 within the vena cava. After deployment of the expanded filter 200 within the vena cava the catheter 102 is withdrawn as shown in FIG. 6C, and the filter elutes drug as described herein.

In one embodiment, the medical device of the present invention, such as the drug-coated stent or lumen filter, can be utilized to locally deliver the drug as described herein. As such, the medical device can be used as a drug delivery system instead of or in concurrence to being a stent or a lumen filter.

In one embodiment, the medical device of the present invention, such as the drug-coated stent or lumen filter, can be configured to systemically elute the drug in an amount sufficient for maintaining a therapeutically effective amount of drug in the blood. For example, everolimus, zotarolimus, or other rapamycin analogs can be included in the polymeric coating of the medical device in an amount that systemically delivers the drug into the blood stream for systemic administration. The amount of drug elution can be configured to be sufficient for providing the therapeutic benefit of the drug for the treatment and/or prophylaxis in which the drug is being used. Such amounts are readily obtainable and the blood concentration can be achieved by altering (e.g., increasing or decreasing) the total amount of drug in the polymer.

In one embodiment, the medical device, such as the lumen filter, can be configured for substantially systemic drug delivery in addition to and/or instead of local delivery into the adjacent tissue. In such a configuration, the medical device is configured to preferentially elute the drug into the blood over the tissue. This can be accomplished by any of the following: applying the drug-loaded polymer to at least one fluid-contacting surface of the medical device; coating the tissue-contacting surfaces of the medical device with a coating that inhibits drug diffusion; and combinations thereof.

In one embodiment, the medical device, which can be in the form of a stent, lumen filter, implant, or the like, can be configured as a drug delivery system that can be a substitute for an oral medication regimen. This can be achieved by the medical device in a suitable form for implantation into a body cavity, lumen, organ, subcutaneous, or any other body part. Many medical devices are configured specifically for placement in the body and any of these medical devices can be configured for controlling drug elution so as to obtain a desired systemic concentration via the configurations described herein. That is, the drug-loaded polymer that has a long term elution profile can be selectively applied to the medical device. As such, the medical device becomes a systemic drug release device instead of a device to treat an area of stenosis. The drug release device could replace daily pills for individuals in need of the therapy provided by the drug, such as transplant patients. However, any drug for any condition can be applied to the medical device in the polymer system described herein for treatment of any disease.

EXAMPLES

Example 1

Stent in vivo experimental pharmacokinetics of the peripheral everolimus eluting self-expanding nitinol stent (i.e., STENT A) were assessed in the porcine model. Briefly, stents were implanted in the iliofemoral arteries, explanted at pre-determined endpoints, and assayed for drug content by HPLC. The results (e.g., FIG. 2A) showed that the drug was slowly released from the device over approximately three months, at a rate largely independent of stent configuration. The three-month release rates considerably prolonged as compared to previously developed peripheral drug-eluting stents which elute over about one week (STENT #1) or coronary drug-eluting stents which elute over about one month (STENT #1 and STENT #2).

Example 2

Tissue in vivo experimental pharmacokinetics of the peripheral everolimus eluting self-expanding nitinol stent (i.e., STENT A) in the porcine model. Stents were implanted in the iliofemoral arteries. At pre-determined endpoints, stented arterial tissue was explanted and assayed for drug content by HPLC. Drug content following STENT A implantation, expressed in μg drug/g arterial tissue, is shown in FIG. 2B comparison to porcine coronary drug content after treatment with coronary drug-eluting stents (STENT #2 and STENT #3). The relatively high drug content and slow release profile of the STENT A stent assures that the vessel walls of treated target arteries will comparatively contain more drug for longer periods of time.

Example 3

Figure 3:
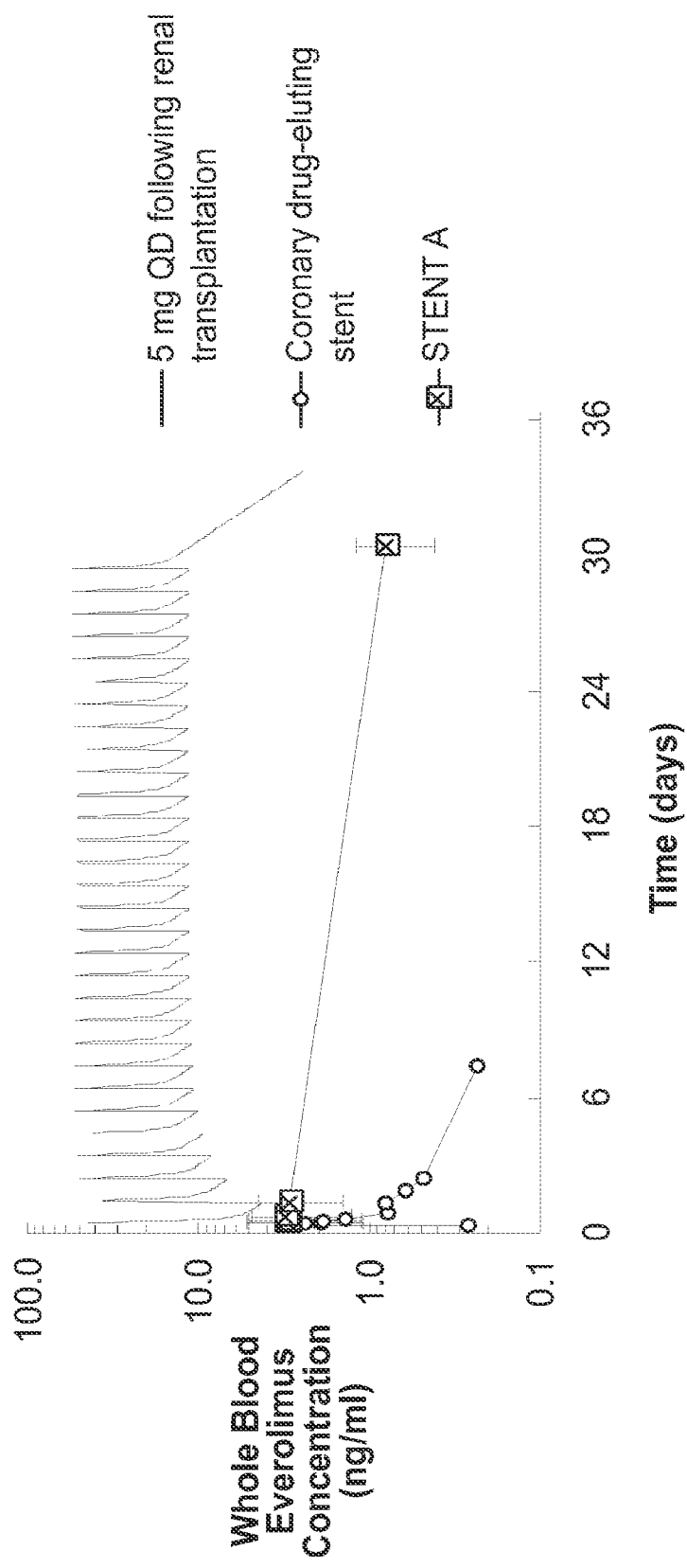
FIG. 3 includes a graph illustrating everolimus blood concentration after drug eluting stent implantation.
Figure 4C:
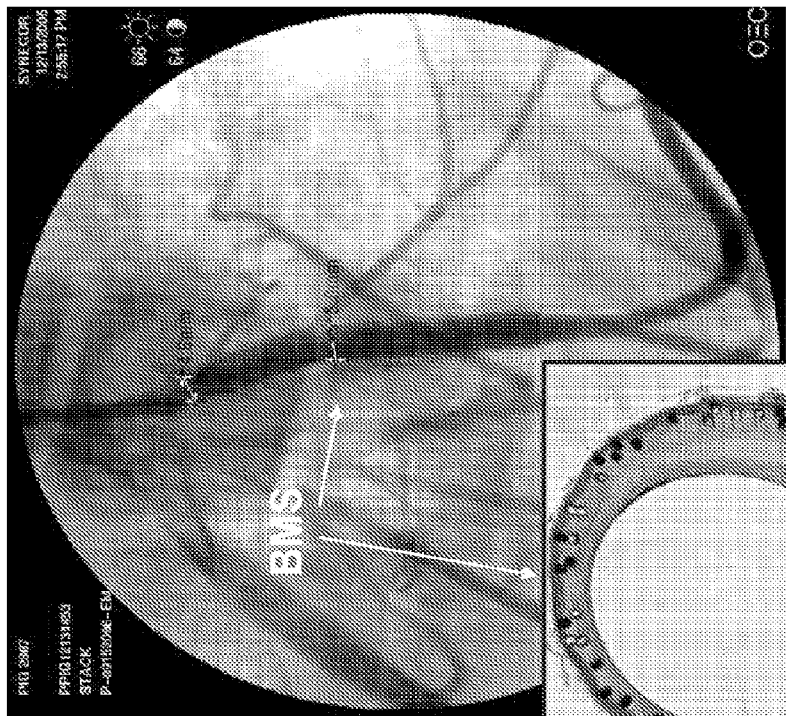
FIGS. 4A-4C include photographs of vessels (FIGS. 4A and 4C) and cross-sections (FIGS. 4B and 4D) of vessels at 90 days after drug eluting stent (DES) (FIGS. 4A and 4B) and bare metal stent (BMS) (FIGS. 4C and 4D) implantation.
Figure 4D:
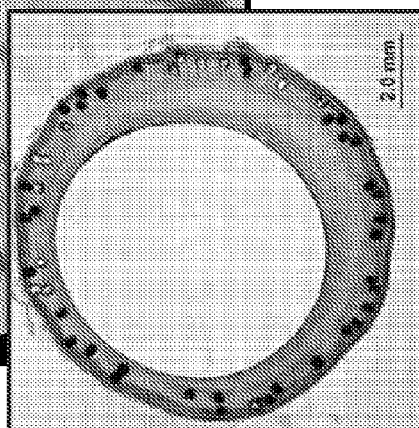
Figure 4B:
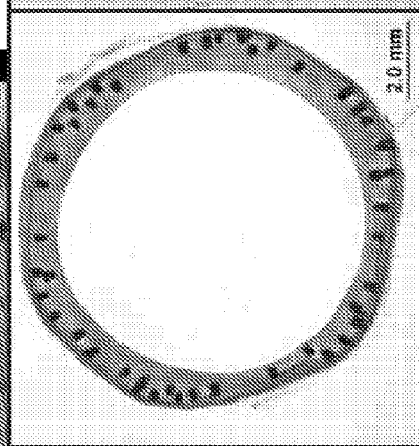
Figure 4A:
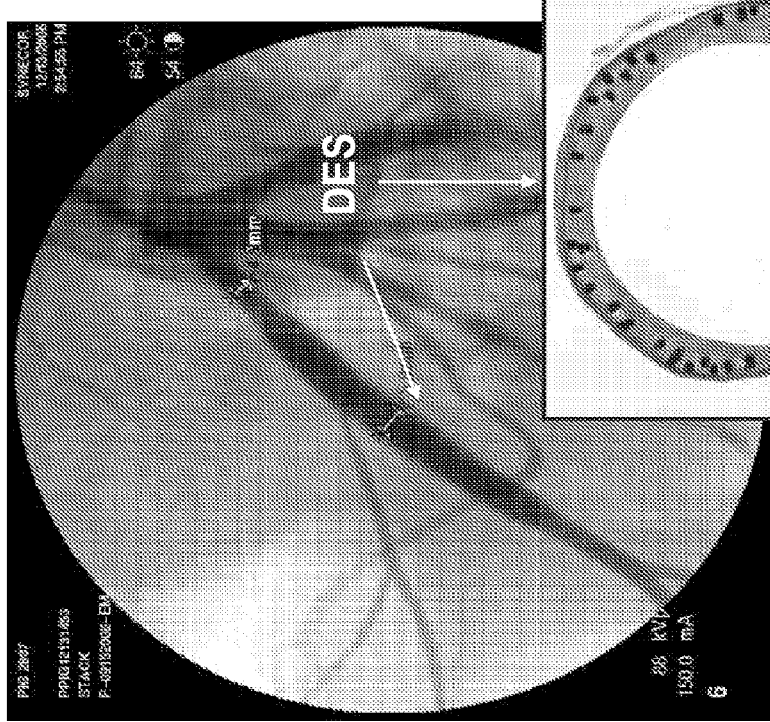

Systemic or blood in vivo experimental pharmacokinetics of the peripheral everolimus-eluting self-expanding nitinol stent (e.g., STENT A) in the porcine model. As shown in FIG. 3, because everolimus is released slowly from the device, the whole blood concentration of everolimus in stented patients is projected to be in the range of 1-6 ng/ml (square-marked line), lower than the recommended upper therapeutic limit in transplanted patients (8 ng/ml) and considerably lower than the $C_{max}$ of patients treated with 5 mg everolimus per day in safety studies (116 ng/ml, zigzag line). Because of its slow release profile, whole blood everolimus concentrations after ABSOLUTE-E stenting approximate those of traditional coronary drug-eluting stents (circle-marked line).

Example 4

Long-term in-vivo angiographic and histologic results of STENT A stenting (DES) vs. bare metal stenting (BMS) were studied. In this study, overlapped DES and BMS were implanted into the right and left iliofemoral arteries of Yucatan Miniature swine. After six months, the stented portion of the arteries were embedded in methylmethacrylate resin, sectioned, ground, polished, and stained with Toluidine Blue and Basic Fuschin stains. As shown in FIG. 4 in the angiographic and histologic examples, the everolimus-eluting DES was effective in limiting neointimal hyperplasia and in-stent restenosis as compared to the BMS.

Example 5

Nitinol stents were coated with EVAL and everolimus. Briefly, N,N-Dimethyl acetamide was used for EVAL polymer formulation at 4.5% (w/w). Everolimus was then formulated with EVAL/DMA to obtain a drug to polymer ratio of about 1:1.6. The permitted daily exposure of DMA was defined as 10.9 mg by ICH Guidelines on Residual Solvents. Additionally, the tests and specifications for DES indicate that DMA residual solvent is not to exceed 40 μg for a stent 8.0×28 mm. The coated stent was sterilized with ethylene oxide.

Example 6

Experiments were conducted in order to determine the in vivo release rate and drug elution profile for the drug eluting stents of the present invention. Briefly, stents of a dimension of 10.0×28 mm having an EVAL coating with everolimus at 1070 μg total drug were implanted into peripheral vasculature of healthy swine. The swine were divided into 5 groups and assays at 3, 7, 14, 28, and 90 days. Concentrations of Everolimus in whole blood and in arterial tissue in the stented vessel were measured and pharmacokinetic parameters of Tmax, Cmax and t1I2 were calculated. The rate of elution from the stent was determined by measuring the amount of drug remaining on the stent at designated times post-implant, up to 90 days. Drug concentrations in tissue from proximal, medial and distal segments of stented arteries were compared to assess the uniformity of elution along the length of the stent.

Prior to surgery, animals were administered clopidogrel bisulphate and salicylic acid, blood was drawn for a baseline clinical pathology (CBC and Chemistry) analysis. Surgical plane anesthesia was and the vasculature was accessed via the carotid artery. A sheath was placed and sutured into position in order to provide access for the test devices to be placed in to the right and left iliac/femoral arteries. A guiding catheter and wire were passed from the carotid to the distal vasculature using fluoroscopy to visualize the movement of the device through the anatomy. Measurements of the vessels were taken and recorded after reaching the desired location. The devices were then deployed into the best-sized vascular region of the left and right iliac/femoral arteries.

At each interim sacrifice, designated animals were prepared for surgery. Whole blood with EDTA was collected for complete blood count (CBC) with differential. A blood smear was prepared. Serum was prepared from whole blood for a standard chemistry panel. A final angiography was performed. The vessels were measured and the data recorded. Animals were euthanized while under anesthesia, using an acceptable method of euthanasia. The vessels containing the stents were then isolated and visually inspected and removed. The artery was removed from the stent and grossly sectioned into three segments (stented region, unstented proximal, unstented distal). The excised vessels were collected into labeled containers and immediately frozen and stored at (−70° C.).

Analysis of drug concentration in blood and arterial tissue was performed. The method for analysis of Everolimus in porcine whole blood and tissues involves adding 200 µL of internal standard (IS)/precipitating solution to 100 µL whole blood or tissue homogenate. Samples are vortexed and centrifuged. Two hundred microliters of the supernatant is transferred to an autosampler vial. Analysis is performed by injecting 100 µL of sample onto a Zorbax™ SB-C18 (4.6×12.5 mm 5 µm) cleanup column (ambient, 5 mL/min) and then switched to an Inertsil® ODS-3 (2.1×50 mm, 5 µm) analytical column (0.4 mL/min), maintained at 65° C. The sample is loaded onto the cleanup column using a mobile phase of 50/50 methanol/0.1% formic acid with 0.2 mM NaCl. Isocratic elution from the analytical column is performed using a mobile phase of 65/35 acetonitrile/0.1% formic acid containing 0.2 mM NaCl. Run time is about 6 minutes. Detection is by mass spectroscopy. The range of the assay is 0.1-100 ng/mL in porcine whole blood and 0.5-500 ng/g in tissue.

Analysis of drug remaining on excised stents was performed. To determine the amount of drug remaining on excised stents, each explanted stent was sonicated at ambient temperature for 15 minutes in 3.5-13 ml N,N-Dimethyl Acetamide (DMA) to elute the drug polymer from the stent. An aliquot of extract is then diluted to a final composition of 50% DMA, 50% water, by volume. Analysis is performed by injecting 50 µl onto a C18 (3×150 mm, 5 µm particle size) column and a UV or photodiode array detector. The isocratic mobile phase is composed of 50/50 (v/v) Acetonitrile/water at 1.2 mL/min. The column temperature is maintained at 50° C. while the samples are maintained at 50° C., and the chromatographic analysis is monitored at 277 nm. Run time is about 25 minutes. The range of the assay is 2.5-60 µg/ml in DMA/water stent extract. Using this method, the total amount of drug is determined as the sum of both 6 and 7 member ring isomers of Everolimus. The amount of drug release in-vivo at each time interval is calculated by subtracting residual drug from the theoretical amount target total content of drug on the stent. The in-vivo release rates are reported as percent of target total content.

The drug concentration in whole blood at each interim time point was determined to be as follows: 0.72 ng/ml at 7 days; 0.23 ng/ml at 14 days; 0.12 ng/ml at 28 days, and below 0.1 ng/ml at 90 days. The drug concentration in tissues in proximity (e.g., proximal to stented region, stented region, and distal to stented region) to the stent at each interim time point was determined to be as follows: at 3 days proximal to stented region was 100 ng/g, stented region was 6607 ng/g, and distal to stented region was 278 ng/g; at 7 days proximal to stented region was 37 ng/g, stented region was 5104 ng/g, and distal to stented region was 208 ng/g; at 14 days proximal to stented region was 40 ng/g, stented region was 4137 ng/g, and distal to stented region was 251 ng/g; at 28 days proximal to stented region was 12 ng/g, stented region was 3928 ng/g, and distal to stented region was 86 ng/g; and at 90 days proximal to stented region was 7 ng/g, stented region was 2303 ng/g, and distal to stented region was 8 ng/g.

The amount of drug remaining on each excised stent was measured by HPLC with spectrophotometric detection. The percent of drug released was then calculated as the amount eluted from the excised stent, subtracted from the Target Total Content (TTC) as specified for the device product (1070 µg dose), divided by the TTC and multiplied by 100. The percentage of Everolimus released from the stent at each timepoint is summarized as follows: at day 3, drug remaining on stent was 900 µg and percent released was 15.9%; at day 7, drug remaining on stent was 758 µg and percent released was 29.1%; at day 14, drug remaining on stent was 577 µg and percent released was 46.1%; at day 28, drug remaining on stent was 388 µg and percent released was 63.7%; and at day 90, drug remaining on stent was 150 µg and percent released was 86.0%. The time at which 50% of the drug has been released is described here as $t_{1/2}$ and was calculated to be 16.3 days. This corresponds to 67 days post-implantation for 1070 µg dose stents to achieve 80% elution. Additionally, the percent drug released over time was compared for stents implanted in the left or right iliac artery. Placement of the stent (in the left or right iliac artery) did not alter the rate of drug release. The percent Everolimus released over time was similar between stents implanted in the left and right iliac arteries.

This study defined blood, tissue, and stent kinetic parameters for 1070 µg dose 10.0×28 mm stents in a porcine model. These results indicate that the Everolimus coated 10.0×28 mm drug eluting stent will provide local, time-limited delivery of drug.

Example 7

The in vivo release rate profile for everolimus from an 8.0×28 mm drug eluting stent coated with EVAL and everolimus in the peripheral vasculature of healthy swine was studied. Concentrations of everolimus in whole blood and in arterial tissue in the stented vessel were measured and pharmacokinetic parameters of Tmax, Cmax and $t_{1/2}$ were calculated. The rate of elution from the stent was determined by measuring the amount of drug remaining on the stent at designated times post-implant, up to 180 days. From these data, the rate of elution was calculated. The test article was a nitinol stent (i.e., STENT A), which was implanted with a 120 cm delivery system. The stent is coated with an ethylene vinyl alcohol co-polymer (i.e., EVAL) containing the drug everolimus at 1070 µg and 3209 µg target total content (henceforth referred to as dose). These doses correspond to approximate nominal concentration per surface area values of 225 µg/cm$^2$ and 675 µg/cm$^2$, respectively. The drug eluting stents were prepared substantially as described herein.

Animals were divided into three groups. Days 3, 7, 28, 56, and 90 were identified as interim time-points for determination of kinetic parameters of drug release. For select groups, additional time-points were added. Group 1 (e.g., 1070 µg) was additionally sampled at day 1, 14, 56, and 180. Group 2 (e.g., 1070 µg different formulation) was additionally sampled at day 56, and group 3 (e.g., 3209 µg was additionally sampled at day 14. Stents were deployed in four vessels per animal (both left and right iliac/femoral region and lateral circumflex femoral region). Implantation and analyses of drug elution were performed substantially as described herein.

The drug concentration for group 1 in whole blood at each interim time point was determined to be as follows: 2.29 ng/ml at 1 day; 2.14 ng/ml at 3 days; 1.07 ng/ml at 7 days; 0.27 ng/ml at 14 days; 0.13 ng/ml at 28 days; and below 0.1 ng/ml at 56 and 90 days. The drug concentration for group 2 in whole blood at each interim time point was determined to be as follows: 2.70 ng/ml at 3 days; 1.57 ng/ml at 7 days; and below 0.1 ng/ml at 28, 56, and 90 days. The drug concentration for group 3 in whole blood at each interim time point was determined to be as follows: 3.35 ng/ml at 3 days; 1.45 ng/ml at 7 days; 1.03 ng/ml at 14 days; 0.29 ng/ml at 28 days; and below 0.1 ng/ml at 56 and 90 days.

The drug concentration in tissues in proximity (e.g., proximal to stented region, stented region, and distal to stented region) to the stent for group 1 at each interim time point was determined to be as follows: at 1 day, proximal to stented region was 403 ng/g, stented region was 9965 ng/g, and distal to stented region was 874 ng/g; at 3 days, proximal to stented region was 199 ng/g, stented region was 12946 ng/g, and distal to stented region was 870 ng/g; at 7 days, proximal to stented region was 159 ng/g, stented region was 10880 ng/g, and distal to stented region was 739 ng/g; at 14 days, proximal to stented region was 105 ng/g, stented region was 6415 ng/g, and distal to stented region was 296 ng/g; at 28 days, proximal to stented region was 66 ng/g, stented region was 5834 ng/g, and distal to stented region was 152 ng/g; at 56 days, proximal to stented region was 19 ng/g, stented region was 833 ng/g, and distal to stented region was 9 ng/g; at 90 days, proximal to stented region was 12 ng/g, stented region was 833 ng/g, and distal to stented region was 9 ng/g; at 180 days, proximal to stented region was 4 ng/g, stented region was 209 ng/g, and distal to stented region was 6 ng/g.

The drug concentration in tissues in proximity (e.g., proximal to stented region, stented region, and distal to stented region) to the stent for group 2 at each interim time point was determined to be as follows: at 3 days proximal to stented region was 533 ng/g, stented region was 8709 ng/g, and distal to stented region was 1552 ng/g; at 7 days, proximal to stented region was 104 ng/g, stented region was 3594 ng/g, and distal to stented region was 435 ng/g; at 28 days, proximal to stented region was 50 ng/g, stented region was 1853 ng/g, and distal to stented region was 73 ng/g; at 56 days, proximal to stented region was 10 ng/g, stented region was 2191 ng/g, and distal to stented region was 25 ng/g; and at 90 days, proximal to stented region was 16 ng/g, stented region was 1271 ng/g, and distal to stented region was 11 ng/g.

The drug concentration in tissues in proximity (e.g., proximal to stented region, stented region, and distal to stented region) to the stent for group 3 at each interim time point was determined to be as follows: at 3 days, proximal to stented region was 520 ng/g, stented region was 22027 ng/g, and distal to stented region was 856 ng/g; at 7 days, proximal to stented region was 698 ng/g, stented region was 17200 ng/g, and distal to stented region was 910 ng/g; at 14 days, proximal to stented region was 307 ng/g, stented region was 16528 ng/g, and distal to stented region was 1119 ng/g; at 28 days, proximal to stented region was 136 ng/g, stented region was 13243 ng/g, and distal to stented region was 414 ng/g; and at 90 days proximal to stented region was 55 ng/g, stented region was 2458 ng/g, and distal to stented region was 63 ng/g.

The percentage of everolimus released from the stent at each time-point is summarized in Table 1.

TABLE 1

| | Average Drug Release From Stent | | | | | |
|---|---|---|---|---|---|---|
| | Group 1 1070 µg Drug Solution Lot #1 | | Group 2 1070 µg Drug Solution Lot #2 | | Group 3 3209 µg | |
| Time (days) | Drug Remaining on Stent (µg)* | Percent Released (%)* | Drug Remaining on Stent (µg)* | Percent Released (%)* | Drug Remaining on Stent (µg)* | Percent Released (%)* |
| 1 | 1000 (23) | 6.5 (0.6) | N/A | N/A | N/A | N/A |
| 3 | 866 (48) | 19.1 (1.4) | 813 (40) | 24.0 (4.5) | 2788 (107) | 13.1 (3.3) |
| 7 | 663 (33) | 38.0 (0.1) | 705 (27) | 34.1 (0.9) | 2545 (47) | 20.8 (1.5) |
| 14 | 484 (82) | 54.8 (4.9) | N/A | N/A | 2132 (60) | 33.6 (1.9) |
| 28 | 311 (69) | 70.9 (2.3) | 299 (28) | 72.1 (1.4) | 1427 (42) | 55.6 (1.3) |
| 56 | 185 (35) | 82.7 (1.4) | 180 (18) | 83.2 (0.1) | N/A | N/A |
| 90 | 123 (39) | 88.5 (3.3) | 120 (20) | 88.8 (1.0) | 411 (86) | 87.2 (2.7) |
| 180 | 34 (11) | 96.9 (0.4) | N/A | N/A | N/A | N/A |

*Reported as Mean (Standard Deviation)
N/A = Not Applicable. This dose/time-point not included in study design.

For groups 1 and 2, $t_{1/2}$ was 11.70 and 11.51 days, respectively, confirming that Lots #1 and #2 of the 1070 µg dose stents were comparable in elution rates. For group 3, the time at which approximately 50% of the drug had been released from the stent was calculated as 21.26 days. This corresponds to 50-58 days post-implantation for 1070 µg dose stents to achieve 80% elution, and approximately 80 days post-implantation for 3209 µg dose stents to achieve the same.

This study defined blood, tissue, and stent kinetic parameters for 1070 µg dose and 3209 µg dose stents in a porcine model. This study demonstrated comparable blood and tissue concentrations, and comparable stent elution rates between lots of 1070 µg dose stents. These results indicate that the Everolimus coated 8.0×28 mm drug eluting stent will provide local, time-limited delivery of drug.

Example 8

The in vivo release rate profile for everolimus from a 7.0× 100 mm drug eluting stent coated with EVAL and everolimus in the peripheral vasculature of healthy swine was studied. Implantation and analyses of drug elution were performed substantially as described herein. The drug concentration in whole blood at each interim time point was determined to be as follows: below 0.1 ng/ml at implantation; 9.56 ng/ml at 0.04 days; 6.25 ng/ml at 0.12 days; 4.97 ng/ml at 0.25 days;

4.94 ng/ml at 1 day; 4.13 ng/ml at 2 days; 3.52 ng/ml at 3 days; 1.64 ng/ml at 7 days; 1.14 ng/ml at 14 days; 0.27 ng/ml at 28 days; and below 0.1 ng/ml at 90 days.

The drug concentration in tissues in proximity (e.g., non-stented region proximal to stented region (A), proximal stented region (B), medial stented region (C), distal stented region (D), and non-stented region distal to stented region(E)) to the stent at each interim time point was determined to be as shown in Table 2.

TABLE 2

Mean Arterial Tissue Concentration by Location

| Time (days) | Concentration (ng/g) | | | | |
|---|---|---|---|---|---|
| | A | B | C | D | E |
| 3 | 269 | 10892 | 16347 | 12357 | 263 |
| | (186) | (4469) | (5005) | (4519) | (202) |
| 7 | 524 | 7894 | 11431 | 9633 | 332 |
| | (302) | (1899) | (1840) | (6373) | (156) |
| 14 | 123 | 4825 | 5243 | 6528 | 353 |
| | (63) | (1303) | (1945) | (1253) | (106) |
| 28 | 114 | 3625 | 4148 | 4275 | 245 |
| | (143) | (810) | (1739) | (828) | (209) |
| 90 | 50 | 2211 | 2699 | 2401 | 18 |
| | (90) | (532) | (657) | (413) | (13) |

Reported as Mean (Standard Deviation)

The drug concentration in extravascular tissue (liver, lung, kidney, gastrocnemius muscle) are summarized in Table 3.

TABLE 3

Extravascular Drug Concentrations

| Group | Time-point | Extravascular tissue (ng/g) | | | | |
|---|---|---|---|---|---|---|
| | | Liver | Spleen | Lung | Kidney | Muscle |
| 1 | 3 Days | 15.1 | 23.1 | 22.8 | 25.6 | 13.5 |
| | | (2.0) | (4.9) | (2.7) | (2.3) | (1.4) |
| 2 | 7 Days | 13.2 | 14.4 | 12.0 | 15.6 | 6.3 |
| | | (0.7) | (3.1) | (0.4) | (1.0) | (1.3) |
| 3 | 14 Days | 8.2 | 11.8 | 8.7 | 11.2 | 4.8 |
| | | (1.4) | (5.0) | (2.6) | (1.7) | (2.2) |
| 4 | 28 Days | 2.9 | 3.5 | 3.2 | 4.2 | 0.8 |
| | | (0.7) | (0.7) | (1.1) | (0.7) | (0.2) |
| 5 | 90 Days | BLLOQ | 0.7 | 0.5 | 0.8 | BLLOQ |
| | | | (0.1) | (0.0) | (0.0) | |

Reported as Mean (Standard Deviation)
BLLOQ = Below Lower Limit of Quantification (0.5 ng/g)

Maximum tissue concentrations were observed at Day 3 post-implantation for all extravascular tissues sampled. Cmax tissue values for liver, spleen, lung, kidney and gastrocnemius muscle were 15.1, 23.1, 22.8, 25.6, and 13.5 ng/g, respectively. Drug concentrations in kidney, lung and spleen were not significantly different from each other and were significantly greater than liver and gastrocnemius muscle drug concentrations at Day 3 post-implantation (spleen versus liver $p<0.01$, all other $p<0.001$). Liver and muscle drug concentrations were not significantly different from each other. In all tissues except liver, Day 7 post-implantation drug concentrations were significantly less than at Day 3 ($p<0.001$). Drug concentrations in gastrocnemius muscle were significantly less than all other extravascular tissues sampled ($p<0.001$). At Day 14 post-implantation, drug concentration in muscle were significantly lower than in kidney or spleen ($p<0.01$). Drug concentration in kidney was significantly lower at Day 14 than at Day 7 ($p<0.05$). In liver, drug concentration at Day 14 was also significantly lower than at Day 7 ($p<0.05$). In all extravascular tissues, drug concentration was significantly lower at Day 28 post-implantation than at Day 14 post-implantation ($p<0.05$ muscle, all other $p<0.001$). At Day 28 post-implantation, drug concentration in gastrocnemius muscle was significantly lower at Day 28 post-implantation than all other extravascular tissues sampled at this time-point ($p<0.001$). At Day 28 post-implantation, drug concentration in kidney was significantly greater than in liver ($p<0.05$). At Day 90 post-implantation, drug concentrations in liver and gastrocnemius muscle were below the lower limit of quantification. In kidney, lung, and spleen, drug concentrations were significantly lower at 90 Days post-implantation than at Day 28 post-implantation (spleen $p<0.01$, kidney and lung $p<0.001$). There were no significant differences in measured drug concentrations between kidney, lung, or spleen at Day 90 post-implantation.

The percentage of everolimus released from the stent and amount remaining on the stent at each time-point is represented in Table 4.

TABLE 4

Average Drug Release From Stent

| Time (days) | Drug Remaining on Stent (μg) | Percent Released (%) |
|---|---|---|
| 3 | 33.39 | 12 |
| | (179) | |
| 7 | 2767 | 27 |
| | (163) | |
| 14 | 2212 | 41 |
| | (49) | |
| 15 | 1859 | 51 |
| | (148) | |
| 16 | 2258 | 40 |
| | (3) | |
| 27 | 1537 | 59 |
| | (37) | |
| 28 | 1613 | 57 |
| | (239) | |
| 90 | 754 | 80 |
| | (133) | |

The time at which 50% of the drug has been released is described here as $t_{1/2}$ and was achieved by approximately 19.8 days post-implantation. By 85.5 days post-implantation, 80 percent of the drug on average had eluted from the stent. Using a porcine model, this study demonstrated everolimus distribution into extravascular tissues, with disappearance of drug from these tissues following the rate of disappearance of everolimus from blood. In vascular tissue, drug was found in segments immediately adjacent and within stented regions, and from unstented vessels. Vascular and nonvascular tissue concentrations decreased over time, indicating no tissue accumulation. These results indicate that the everolimus coated 7.0×100 mm drug eluting stent will provide local, time-limited delivery of drug.

Example 9

The concentration of drug can range between 10 μg/cm$^2$ and 200 μg/cm$^2$, and the stent can range from 20 mm to 300 mm. Accordingly, Table 5 provides for the total amount of drug loaded on the stent as related to the drug amount per area and the stent length.

TABLE 5

| Drug Conc. | Total Dose (μg) | | | |
| --- | --- | --- | --- | --- |
| μg/cm² | 20 mm | 100 mm | 150 mm | 300 mm |
| 10 | 34 | 169 | 253 | 506.6667 |
| 100 | 338 | 1689 | 2533 | 5066.667 |
| 200 | 676 | 3378 | 5067 | 10133.33 |
| 500 | 1689 | 8444 | 12667 | 25333.33 |
| 1000 | 3378 | 16889 | 25333 | 50666.67 |
| 2000 | 6756 | 33778 | 50667 | 101333.3 |
| 225 | 760 | 3800 | 5700 | 11400 |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein in their entirety by specific reference.

What is claimed is:

1. A method of treating peripheral vascular disease in a subject, the method comprising:
    implanting in a peripheral artery of a subject a drug eluting stent comprising:
        a self-expanding stent body of 130 mm to 170 mm in length, the self-expanding stent body being a design of annular elements and interconnectors where the annular elements are connected adjacently by at least one interconnector;
        a polymeric coating disposed on the stent body, the polymeric coating being 2 μm to 50 μm in thickness;
        a lipophilic drug disposed in the polymeric coating, the lipophilic drug being present at an amount between about 4 mg to about 8 mg;
    wherein the maximum systemic blood concentration of the lipophilic drug in the subject is about 30 ng/ml or less than 30 ng/ml.

2. The method as in claim 1, wherein the lipophilic drug is present in an amount greater than or equal to 200 μg/cm².

3. The method as in claim 1, wherein the lipophilic drug is everolimus, zotarolimus, tacrolimus, paclitaxel, or a combination thereof.

4. The method as in claim 3, wherein the lipophilic drug is present at an amount between about 5 mg and about 7 mg.

5. The method as in claim 1, wherein the lipophilic drug is present at an amount between about 5 mg and about 7 mg.

6. The method as in claim 1, wherein the polymeric coating ranges from about 4 μm to about 25 μm in thickness.

7. The method as in claim 1, wherein the polymeric coating comprises a primer layer disposed on the stent body, a drug-loaded layer disposed on the primer layer, and a topcoat layer disposed on the drug-loaded layer.

8. The method as in claim 7, wherein the polymeric coating is characterized by at least one of the following:
    the primer layer being from about 1% to about 20% of the total coating thickness;
    the drug-loaded layer being from about 25% to about 90% of the total coating thickness; or
    the topcoat being from about 5% to about 50% of the total coating thickness.

9. The method as in claim 8, wherein the stent body is nitinol, the lipophilic drug is everolimus, and the polymer of the polymeric coating is an ethylenevinylalcohol copolymer.

10. The method as in claim 1, wherein the lipophilic drug is everolimus.

11. The method as in claim 1, wherein the maximum systemic blood concentration of the lipophilic drug in the subject is about 20 ng/ml or less than 20 ng/ml.

12. The method as in claim 1, wherein the maximum systemic blood concentration of the lipophilic drug in the subject is about 10 ng/ml or less than 10 ng/ml.

13. The method as in claim 1, wherein the stent body is formed from Nitinol.

14. The method as in claim 1, wherein the stent is implanted in a superficial femoral artery.

15. The method as in claim 1, wherein the stent is implanted in an iliofemoral artery.

16. A method of treating peripheral vascular disease in a subject, the method comprising:
    implanting in a peripheral artery of a subject a drug eluting stent comprising:
        a self-expanding stent body of Nitinol, the self-expanding stent body being a design of annular elements and interconnectors where the annular elements are connected adjacently by at least one interconnector;
        a polymeric coating disposed on the stent body, the polymeric coating being 5 μm to 20 μm in thickness; and
        everolimus disposed in the polymeric coating;
    wherein the maximum systemic blood concentration of everolimus in the subject is about 30 ng/ml or less than 30 ng/ml;
    and
    wherein
        the stent is 28 mm in length and 10 mm in diameter, and the amount of everolimus is about 1.07 mg; or
        the stent is 100 mm in length and 7 mm in diameter, and the amount of everolimus is about 3.5 mg.

17. The method as in claim 16, wherein the stent is 100 mm in length and 7 mm in diameter.

18. The method as in claim 16, wherein the stent is 28 mm in length and 10 mm in diameter.

19. The method as in claim 18, wherein the peripheral artery of the subject is a superficial femoral artery.

20. The method as in claim 18, wherein the peripheral artery of the subject is an iliofemoral artery.

21. The method as in claim 17, wherein the peripheral artery of the subject is a superficial femoral artery.

22. The method as in claim 17, wherein the peripheral artery of the subject is an iliofemoral artery.

* * * * *